US011458189B2

(12) United States Patent
Berna et al.

(10) Patent No.: US 11,458,189 B2
(45) Date of Patent: Oct. 4, 2022

(54) CYTOPROTECTIVE DRUGS

(71) Applicant: BALMES TRANSPLANTATION, Marseilles (FR)

(72) Inventors: Patrick Berna, Cassis (FR); Méryl Thomas, Saint-Just-Saint-Rambert (FR); Gwenaelle Antetomaso, Garons (FR)

(73) Assignee: BALMES TRANSPLANTATION, Marseilles (FR)

( * ) Notice: Subject to any disclaimer, the term of this patent is extended or adjusted under 35 U.S.C. 154(b) by 0 days.

(21) Appl. No.: 16/764,618

(22) PCT Filed: Nov. 16, 2018

(86) PCT No.: PCT/FR2018/052890
§ 371 (c)(1),
(2) Date: May 15, 2020

(87) PCT Pub. No.: WO2019/097187
PCT Pub. Date: May 23, 2019

(65) Prior Publication Data
US 2020/0397854 A1 Dec. 24, 2020

(30) Foreign Application Priority Data
Nov. 17, 2017 (FR) ...................................... 1760882

(51) Int. Cl.
*A61K 38/12* (2006.01)
*A61P 9/10* (2006.01)
*A01N 1/02* (2006.01)
*A61K 31/519* (2006.01)

(52) U.S. Cl.
CPC ............ *A61K 38/12* (2013.01); *A01N 1/0226* (2013.01); *A61K 31/519* (2013.01); *A61P 9/10* (2018.01)

(58) Field of Classification Search
None
See application file for complete search history.

(56) References Cited

PUBLICATIONS

Patil et al. "Echinocandins in antifungal pharmacotherapy," Journal of Pharmacy and Pharmacology, 69 (2017), pp. 1635-1660 (Year: 2017).*
Wang et al. "Human autoimmune diseases: a comprehensive update," Journal of Internal Medicine, 2015, 278; 369-395 (Year: 2015).*
Binytha Wegner et al., "Caspofungin is less nephrotoxic than amphotericin B in vitro and predominantly damages distal renal tubular cells", Nephrology Dialysis Transplantation, pp. 2071-2079, vol. 20. No. 10. (Jul. 5, 2005).
Stover et al., "Cardiac toxicity of some echinocandin antifungals", Expert Opinion on Drug Safety, pp. 5-14, vol. 13. No 1. (Sep. 18, 2013).
Peter et al., "Micafungin-Induced Suicidal Erythrocyte Death", Cellular Physiology and Biochemistry, pp. 584-595 vol 39. No. 2 (Jan. 1, 2016).
Saliba et al., "Randomized Trial of Micafungin for the Prevention of Invasive Fungal Infection in High-Risk Liver Transplant Recipients", Clinical Infectious Diseases, pp. 997-1006, vol. 60. No. 7 (Dec. 17, 2014).
Kimakura et al., "Toxicity of Topical Antifungal Agents to Stratified Human Cultivated Corneal Epithelial Sheets", Journal of Ocular Pharmacology and Therapeutics, pp. 810-814, vol. 30. No. 10 (Dec. 1, 2014).
Olson et al., "Differences in efficacy and cytokine profiles following echinocandin or liposomal amphotericin B monotherapy or combination therapy for murine pulmonary or systemic aspergillus flavus infections", Antimicrobial Agents and Chemotherapy, pp. 218-230, vol. 56. No. 1 (Oct. 3, 2011).
Anonymous., "Highlights of Prescribing Information These highlights do not include all the information needed to use MYCAMINE safely and effectively. See Full Prescribing Information for", <URL:https://www.accessdata.fda.gov/drugsatfda/docs/label/2008/021506s008lbl.pdf> (Jan. 31, 2008).
Anonymous, "Final Package Insert for ERAXIS (anidulafungin) for Injection [Intravenous Infusion] (not for IV Bolus Injection) Rx Only", Retrieved from the Internet: <URL:https://www.accessdata.fda.gov/drugsatfda/docs/label/2006/021632s000.021948sOOOlbl.pdf>(Feb. 15, 2006).
Winkler et al., "Caspofungin for post solid organ transplant invasive fungal disease: results of a retrospective observational study: Caspofungin in SOT patients", Transplant Infectious Disease, pp. 230-237, vol. 12. No. 3. (Jun. 1, 2010).
Wezensky et al., "Implications of hypoxic microenvironments during invasive aspergillosis", Medical Mycology, pp. S120-S124, vol. 49. No. S1 (Apr. 1, 2011).
Kernt et al., "Intraocular caspofungin: in vitro safety profile for human ocular cells : In vitro safety of intraocular caspofungin", MYCOSES, pp. e110-e121, vol. 54. No. 4 (Feb. 19, 2010).

* cited by examiner

*Primary Examiner* — Christina Bradley
(74) *Attorney, Agent, or Firm* — Browdy and Neimark, PLLC

(57) ABSTRACT

The invention relates to compounds of the echinocandin family or a semi-synthetic derivative thereof or a salt thereof or an ester thereof, or an ester salt thereof, intended to be used as a cytoprotective drug, particularly as a drug for the prevention and/or protection and/or treatment of cell death and/or of degenerative pathological situations or processes which result in cell death, and even more particularly as a drug for the prevention and/or protection and/or treatment of cell death and/or degenerative pathological situations or processes which result in cell death, when they are associated with ischaemia-reperfusion.

9 Claims, 7 Drawing Sheets

CYTOPROTECTIVE DRUGS

The present invention concerns new cytoprotective drugs for use in protecting an individual, particularly an individual at risk, an organ, a tissue, or cells from the consequences of cellular dysfunction.

More particularly, the invention relates to the use of compounds of the echinocandin family as a cytoprotective drug.

In the present text, unless otherwise specified, any occurrence of "compound of the echinocandin family" should be understood as "compound of the echinocandin family or one of its semi-synthetic derivatives or one of their salts (salts of the compounds or salts of the semi-synthetic derivatives) or one of their esters (esters of the compounds or esters of the semi-synthetic derivatives) or one of their ester salts (salts of the esters of the compounds or salts of the esters of the semi-synthetic derivatives)".

Cellular degenerative processes can lead to the reduction and/or disruption of cellular functioning, particularly the loss of one or more of the cell's functions. These cellular degenerative processes can also lead to cell death.

Cells have developed adaptive mechanisms (cytoprotective mechanisms), in response to cellular degenerative processes, which can maintain or restore cellular functions and lead to an extension of their lifespan, thereby delaying cell death.

However, these cytoprotective mechanisms are sometimes insufficient, inadequate, or induced too late, thus failing to prevent the reduction and/or disruption of cellular functioning, particularly the loss of one or more of the cell's functions nor ultimately to delay and/or prevent early cell death.

It can therefore be advantageous to have new drugs, cytoprotectives, which would promote cytoprotection. This is one of the objects of the present invention.

According to the present text, the term "cytoprotective" refers to the ability of agents, for example chemical compounds, whether natural or not, to protect and/or prevent and/or treat cells against the consequences at the cellular level of degenerative processes or pathological situations and particularly those which may lead to cell death.

By "pathological situations" in the present text is meant, unless otherwise specified, for example, diseases or conditions, or traumas, or exposure to various factors, particularly factors triggering cell death processes, but also events for example such as accidental occlusion, hemorrhage and/or medical procedures, particularly surgical procedures, for example such as organ transplants.

By "protect" is meant, according to the invention, prevention of the occurrence, inhibition, reduction or treatment of the consequences at the cellular level of pathological situations or degenerative processes that may lead to cell death, particularly in an individual at risk.

By "treatment" is meant, according to the invention, a treatment that is preventive, advantageously in an individual at risk, and/or curative and/or palliative. It includes the fact of inhibiting and/or eliminating the appearance and/or the development of a pathological situation or of a degenerative process or of reducing the severity of such pathological situation or such degenerative process, such as reducing the number or severity of symptoms associated with the pathological situation or the degenerative process, enhancing the quality of life of the individual suffering from such pathological situation or such degenerative process, decreasing the amounts of other medications needed to treat the pathological situation or the degenerative process, enhancing the effect of another treatment taken to treat the pathological situation or the degenerative process, or prolong the life of individuals suffering from the pathological situation or the degenerative process.

By "preventive" or "prevent" is meant reducing the probability of developing or stopping or delaying the onset of a pathological situation or of a degenerative process in an individual who has not developed, but presents a risk of developing that pathological situation or that degenerative process.

By "at risk" it is meant that an individual has one or more risk factors for a pathological situation or degenerative process, which are measurable parameters that can be correlated with the development of the pathological situation or the degenerative process and are known to the person skilled in the art.

An individual who presents one or more of these risk factors has a higher probability of developing the pathological situation or the degenerative process than an individual who does not present these risk factors. For example, an individual for whom surgery is planned may be considered as an individual at risk.

As a further example, an individual with the following risk factors, hypertension, smoking, carotid artery stenosis, physical inactivity, diabetes mellitus, hyperlipidemia, transient ischemic attack, atrial fibrillation, coronary artery disease, heart failure, history of myocardial infarction, left ventricular dysfunction or mitral stenosis may be considered as an individual with risk factors for stroke and brain tissue ischemia.

The terms "organ", "tissue" or "cells" refer to one or more cells, part of an organ, a whole organ, a tissue or group of tissues (limbs, etc.), of human or animal origin. The invention may potentially be directed to all organs, tissues or cells. Examples are solid organs, such as the liver, lung, heart, kidney, or pancreas, cells such as, among others, the cells of the above-mentioned organs, stem cells, tissues for example such as the skin, cornea, and vascularized composite tissue (VCA). The invention is preferably directed to solid organs and even more preferentially the kidney are targeted by the invention.

Among the main processes of cell death, a distinction can basically be made between cell death such as necrosis, and programmed cell deaths such as apoptosis, ferroptosis, autophagy, parthanatosis, pyroptosis and necroptosis, among others.

Necrosis is a so-called "accidental" cell death that occurs at the time of traumatic tissue damage. It is the plasma membrane of the cell that is most affected, resulting in a modification of the cell's homeostasis. The cells will become engorged with water to the point where this leads to lysis of their plasma membrane. This cell lysis leads to the release of the cytoplasmic contents and membrane fragments into the surrounding environment, which are at the origin of inflammatory processes. This is known as sterile inflammation involving innate immunity.

Necrosis may occur generally further to events such as a major trauma for example a stoppage or reduction in blood flow at an organ, hyperthermia (rise high temperature), poisoning by a chemical product, shock or a physical cut, etc.

One of the most widely known necroses is that of the myocardium during an infarction (interruption of circulatory supply of the heart muscle) due to an obliteration (obstruction) of a coronary artery.

Necrosis, like programmed cell death, can affect a cell, a group of cells, a tissue, a set of tissues, an organ or a group of organs while other parts in the neighborhood stay alive. The resulting transformation is mortification of the cells, tissues or organs.

Programmed cell death, in contrast, represents a programmed cessation of cell function following a detrimental stimulus leading to the death of the cell with a release or a controlled disappearance of its constituents.

The most widely-known form of programmed cell death, apoptosis, is an integral part of the normal physiology of an organism. It is a highly regulated physiological form of cell death. It is necessary for the survival of multicellular organisms and plays a role of the utmost importance during embryogenesis.

Apoptosis usually involves individual cells in a tissue or organ and causes little or no inflammation. One of the characteristic morphological features of apoptosis is the extensive condensation of both the nucleus and cytoplasm which induces a significant decrease in cell volume. The nucleus then fragments, each fragment being surrounded by a double envelope. Apoptotic bodies (cytoplasmic and nuclear elements) are then released and will be absorbed by phagocytosis by neighboring cells.

Apoptosis can be induced in different ways. For example, radiation, the presence of a chemical compound or a hormone are stimuli capable of inducing a cascade of apoptotic or pro-apoptotic events in the cell. Intracellular signals such as incomplete mitosis or DNA damage can also induce apoptosis.

Apoptosis can also occur after the action of a genotoxic or in the course of a disease. Some pathologies are characterized by abnormal apoptosis, leading to the loss of certain cell populations, such as hepatotoxicity, retinopathies, cardiotoxicity.

A distinction is therefore made between physiological and pathological apoptosis. The invention is primarily aimed at pathological apoptosis.

Another mechanism of programmed or regulated cell death, necroptosis, has characteristics of necrosis and apoptosis. A cell dying by necroptosis has characteristics similar to those of a cell dying by necrosis, but the biochemical steps of this mechanism are more similar to those of apoptosis. This mechanism is one of the mechanisms of cell death involved, for example, in ischemia.

There are other cell death processes, such as ferroptosis, which is cell death induced by a release of iron that promotes the generation of harmful free radicals not buffered by the glutathione system. Parthanatosis, another type of programmed cell death, is dependent on poly (ADP-ribose) polymerase 1 (PARP) and apoptosis-inducing factor (AIF).

Pyroptosis is triggered in response to many stimuli, whether they are PAMPs (pathogen-associated molecular patterns) or DAMPs (damage-associated molecular patterns). This is a rapid, caspase-1-dependent cell death and is characterized by plasmic membrane rupture and subsequent release of pro-inflammatory intracellular substances.

Lastly, autophagy includes several lysosomal degradation pathways of cellular components, which are essential for cell homeostasis and may possibly lead to cell death. Deregulation of this process of autophagy may become pathological.

It is therefore one of the aims of the present invention to provide new drugs (compound alone or pharmaceutical composition containing the compound) which could make it possible to protect, prevent and/or treat a cell against cell death or the processes leading thereto, for example necrosis and/or pathological apoptosis and/or pyroptosis and/or necroptosis and/or ferroptosis and/or parthanatosis and/or autophagy (antinecrotic and/or antiapoptotic and/or antipyroptotic and/or antinecroptotic and/or antiferroptotic and/or antiparthanatotic and/or antiautophagic drugs).

Trauma and factors triggering cell death processes can be of physical and/or chemical and/or biological origin.

Physical origins include, for example, exposure to radiation (UV, gamma, X, etc.), impacts, cuts, hyperthermia, hypothermia, or the presence of crystals or foreign bodies in the organism.

Chemical origins include, for example, variations in pH, poisoning by poisons, waste, environmental toxins, free radicals, reactive oxygen. Biological origins include, for example, asphyxia, hypoxia or oxygen deprivation, nutrient deprivation, deprivation of growth factors, poisoning by free radicals or reactive oxygen produced in situ, cell toxins, massive discharges of cytokines or ischemia-reperfusion.

Certain events may also be cited for example such as accidental occlusions, hemorrhage, and certain medical procedures for example such as the use of artificial respirators, balloon inflation, sutures, as well as chemical or biological agents used as therapeutic agents in the context of medical treatments such as cytostatic or cytotoxic agents, immunosuppressant agents, or anti-inflammatory agents.

Surgical procedures that can lead to a process of cell death may be, for example, procedures requiring a transient interruption of blood circulation leading to ischemia or hypoperfusion, local or general (tourniquet, clamp, etc.), for example such as during surgery, particularly angioplastic surgery, for example on the heart or on organs or on the main or peripheral vessels, or cardiac surgery during which it is sometimes necessary to pass around (bypass) the cardiopulmonary system, or to stop the heart, thoracic or vascular surgery, as well as any surgery that requires the voluntary occlusion of an organ, or part of an artery, or a reduction in blood flow through the organ.

Among the most important diseases or conditions that can lead to a process of cell death are, for example:

diseases relating to the circulation such as atherosclerosis, arterial sclerosis, peripheral vascular diseases, peripheral vascular attacks, in particular cerebral, pulmonary or intestinal attacks, aneurysms, chronic venous insufficiency, or varicose veins;

kidney diseases for example such as acute kidney disorders, acute kidney injury, renal ischemia, renal ischemia, glomerulonephritis, acute or chronic interstitial nephropathies, nephroangiosclerosis, diabetic kidney, acute or chronic kidney failure, or side effects of dialysis;

cardiovascular diseases such as cardiac and/or vascular ischemia, myocardial infarction, ischemic heart disease, chronic or acute heart failure, cardiac dysrhythmia, atrial fibrillation, ventricular fibrillation, paroxysmal tachycardia, hypertrophic cardiomyopathy, anoxia, hypoxia, side effects due to therapy with medicinal agents and in particular anti-cancer agents;

neurological diseases such as stroke, transient ischemic attack, prenatal cerebral hypoxia, adult or child cerebral hypoxia and neurodegenerative diseases such as Alzheimer's disease, Parkinson's disease, Huntington's disease, amyotrophic lateral sclerosis and infantile spinal muscular atrophy; muscular diseases such as muscular dystrophy, for example such as Duchenne's muscular dystrophy, myotonic dystrophies, myopathies and myasthenias;

organ-specific or systemic inflammatory or autoimmune diseases, for example such as rheumatoid arthritis, chronic inflammatory intestinal disease, psoriasis, vasculitis, bronchial asthma, chronic obstructive pulmonary disease and eosinophilic sinusitis or systemic lupus;

diseases of the bones, joints, connective tissue and cartilage, for example such as osteoporosis, osteomyelitis, arthritis including for example osteoarthritis and psoriatic arthritis, avascular necrosis, progressive ossifying fibrodysplasia, rickets, Cushing's syndrome;

ischemic attacks or diseases of the limbs, skin diseases, for example such as dermatitis, eczema, psoriasis, aging, or alterations in the healing process;

hematological and vascular diseases such as anemia, vascular amyloidosis, hemorrhages, sickle cell disease, red blood cell fragmentation syndrome, neutropenia, leukopenia, bone marrow aplasia, pancytopenia, thrombocytopenia, and hemophilia;

lung diseases for example such as pneumonia, asthma, chronic obstructive pulmonary diseases for example such as chronic bronchitis and emphysema;

diseases of the gastrointestinal tract, such as ulcers or mesenteric infarction;

liver diseases for example such as hepatitis of viral origin or hepatitis caused by other infectious agents, alcoholic hepatitis, autoimmune hepatitis, fulminant hepatitis, liver fibrosis, cirrhosis, alcoholic liver disease (ALD), liver diseases caused by toxins or drugs; steatoses such as non-alcoholic liver steatoses (NASH), or accompanying exogenous intoxication with alcohol, drugs, or liver ischemia;

metabolic diseases such as diabetes mellitus, diabetes insipidus, glucose intolerance syndrome, obesity, hyperlipidemia, hypothalamic-pituitary axis dysfunction, thyroiditis, abetalipoproteinemia, galactosemia, gout, glycogen disease, Wilson's disease, or Weber-Christian disease;

pancreatic diseases such as acute or chronic pancreatitis;

severe poisoning by chemical or infectious agents, toxins or drugs, for example such as septic shock and its consequences, or iatrogenic diseases;

disorders associated with aging, for example such as accelerated aging syndrome;

dental disorders for example such as those leading to tissue damage for example such as periodontitis;

ophthalmic diseases or disorders for example such as diabetic retinopathies, glaucoma, ptosis, optic atrophy, chronic progressive external ophthalmoplegia, macular degeneration, retinal degeneration, retinitis pigmentosa, retinal holes or tears, retinal detachment, retinal ischemia, acute retinopathies associated with trauma, inflammatory degeneration, post-surgical complications, drug-induced retinopathies, or cataract;

disorders of the auditory pathways, for example such as otosclerosis and antibiotic-induced deafness;

diseases associated with the mitochondria (mitochondrial pathologies), for example such as Friedrich's ataxia or congenital muscular dystrophy with structural mitochondrial abnormalities.

Similarly, the transplantation of organs, tissues or cells may lead to a process of cell death, affecting all or only some of the cells, whether in the organ donor, organ recipient, organ, tissue or cells to be transplanted, before, during (removal, transport, preservation, storage at different temperatures and in a static or dynamic manner and/or its reimplantation) or after transplantation.

Cell death that may occur during organ, tissue or cell transplantation, which may affect only some of the cells of said organ, said tissue or said cells, may lead to delayed or only partial recovery of function of said organ, said tissue or said cells once transplanted.

Pharmacologically active compounds are currently still being sought to act in an individual, particularly an individual at-risk, against the cell death processes that can occur in the pathological situations or degenerative processes mentioned above.

The present invention is a response to this demand for new cytoprotective pharmaceutical compounds or compositions. More particularly, the applicant has discovered that the compounds of the echinocandin family are endowed with remarkable cytoprotective properties.

Echinocandins are cyclohexapeptides produced naturally by fermentation, having a lipophilic acyl group and which can be modified in a more or less complex manner by chemical synthesis (semi-synthesis or hemi-synthesis) to give derivatives which will be designated as semi-synthetic.

Echinocandins are a class of antifungal drugs that inhibit the synthesis of β-glucans in the cell wall of fungi. These β-glucans are not present in mammalian cells, which renders the use of echinocandins in mammals prima facie without risk of side effects.

The echinocandin family includes caspofungin, micafungin, anidulafungin, cilofungin, enfumafungin, arundifungin, echinocandin B, biafungin, CD101 IV or rezafungin, and pneumocandins, arbocandins and papulacandins.

Caspofungin or 1-[(4R,5S)-5-[(2-aminoethyl)amino]-N2-(10,12-dimethyl-1-oxotetradecyl)-4-hydroxy-L-ornithin]-5-[(3R)-3-hydroxy-L-ornithin] pneumocandin B0, (Cas No.: 162808-62-0, 179463-17-3 (diacetate), ATC Code: JO2AX04, Drug Bank: DB00520, PubChem: 468682) has the empirical formula $C_{52}H_{88}N_{10}O_{15}$ and can be represented by the following Formula I:

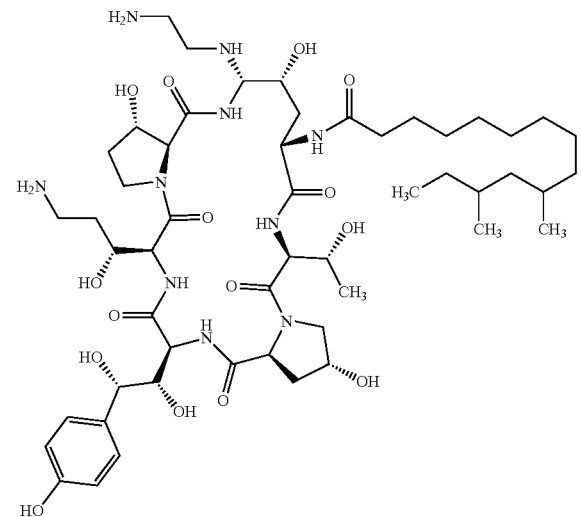

Formula I

Caspofungin acetate is a semi-synthetic lipopeptide synthesized from a fermentation product of *Glarea lozoyensis* and marketed under the brand name Cancidase®.

The fungicidal activity of caspofungin has been demonstrated on *candida*. In vitro and in vivo studies demonstrate that exposure of *aspergillus* to caspofungin causes lysis and death of the ends of the mycelial filaments and sites where cell growth and division occurs. Caspofungin is used in the management of invasive aspergillosis, invasive candidiasis, and suspected fungal infections in cases of febrile neutropenia. Micafungin, or {5-[(1S,2S)-2-[(3S,6S,9S,11R,15S,18S,20R,21R,24S,25S,26S)-3-[(1R)-2-carbamoyl-1-hydroxyethyl]-11,20,21,25-tetrahydroxy-15-[(1R)-1- hydroxyethyl]-26-methyl-2,5,8,14,17,23-hexaoxo-18-[(4-{5-[4-(pentyloxy)phenyl]-1,2-oxazol-3-yl}benzene)amido]-1,4,7,13,16,22-hexaazatricyclo[22.3.0.0]heptacosan-6-yl]-1,2-dihydroxyethyl]-2-hydroxyphenyl}oxidanesulfonic acid (CAS No.: 235114-32-6, ATC Code: J02AX05, DrugBank: DB01141; PubChem: 477468) has the empirical formula $C_{52}H_{71}N_9O_{23}S$ and can be represented by the following formula II:

Anidulafungin is a semi-synthetic echinocandin, a lipopeptide synthesized from a fermentation product of *Aspergillus nidulans*.

Anidulafungin has shown fungicidal activity against *Candida* sp. and activity against the sites of active cell proliferation of the mycelial filaments of *Aspergillus fumigatus*.

Anidulafungin is used in the management of invasive candidiasis in adults.

Formula II

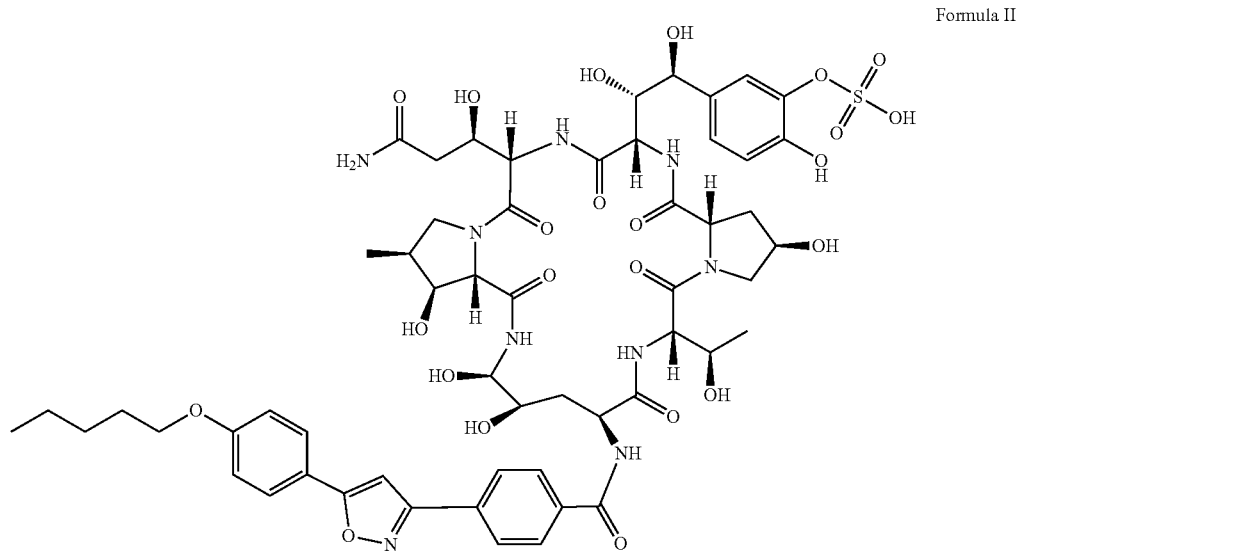 [SMILES: CCCCCOc1ccc(-c2cc(-c3ccc(C(=O)N[C@H]4C[C@@H](O)[C@@H](O)NC(=O)[C@@H]5[C@@H](O)[C@@H](C)CN5C(=O)[C@H]([C@H](O)CC(N)=O)NC(=O)[C@H]([C@H](O)[C@@H](O)c5ccc(O)c(OS(=O)(=O)O)c5)NC(=O)[C@@H]5C[C@@H](O)CN5C(=O)[C@H]([C@@H](C)O)NC4=O)cc3)no2)cc1]

Micafungin has shown fungicidal activity on most species of *candida* and significantly inhibits the active growth of *aspergillus* mycelial filaments.

Micafungin is used in the management of candidiasis.

The sodium form of micafungin is marketed under the brand name Mycamine®.

Anidulafungin, or (N-[(3S,6S,9S,11R,15S,18S,20R,21R,24S,25S,26S)-6-[(1S,2R)-1,2-Dihydroxy-2-(4-hydroxyphenyl)ethyl]-11,20,21,25-tetrahydroxy-3,15-bis[(1R)-1-hydroxyethyl]-26-methyl-2,5,8,14,17,23-hexaoxo-1,4,7,13,16,22-hexaazatricyclo[22.3.0.0]heptacosan-18-yl]-4-{4-[4 (pentyloxy)phenyl]phenyl}benzamide (CAS No. 166663-25-8; ATC Code: J02AX06; PubChem: 166548; DrugBank: DB00362) has the empirical formula $C_{58}H_{73}N_7O_{17}$ and can be represented by the following formula III Anidulafungin is marketed under the brand name Ecalta® in Europe and Eraxis® in Russia and the USA.

CD101 IV or rezafungin may be represented by the following formula IV

Formula IV

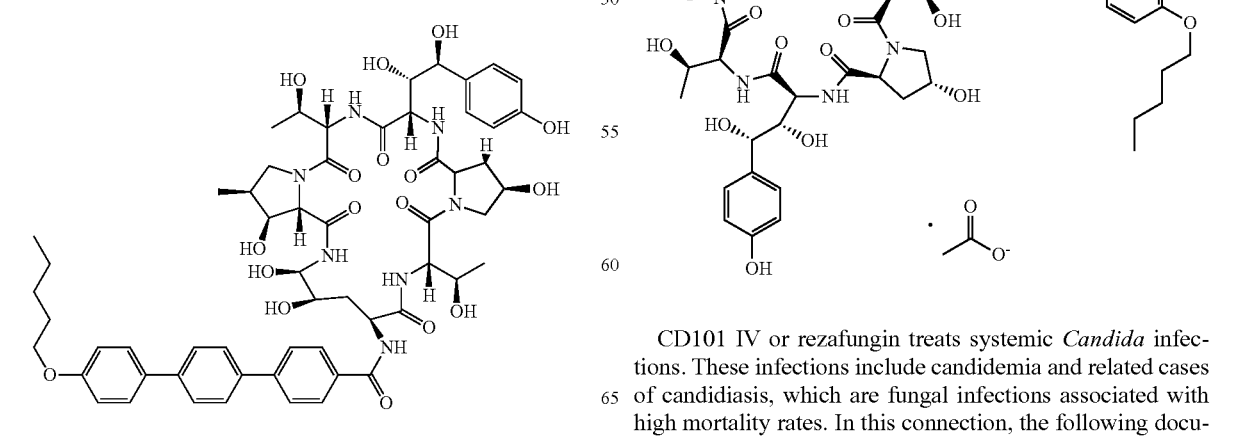

CD101 IV or rezafungin treats systemic *Candida* infections. These infections include candidemia and related cases of candidiasis, which are fungal infections associated with high mortality rates. In this connection, the following documents among others may be cited "Highlights Of Prescribing Information Mycamine", 31 Jan. 2008, Extract from the Internet: URL:https://www.accessdata.fda.gov/drugsatfda_docs/label/2008/021506s00 81bl.pdf.

"Final Package Insert for ERAXIS (anidulafungin) for Injection", 15 Feb. 2006, Extract from the Internet: URL: https://www.accessdata.fda.gov/drugsatfda_docs/label/2006/021632s000,02 1948s000lbl.pdf Binytha Wegner et al.: "Caspofungin is less nephrotoxic than amphotericin B in vitro and predominantly damages distal renal tubular cells", NEPHROL DIAL TRANSPLANT., Vol. 20, No. 10, 5 Jul. 2005, pages 2071-2079, Mikiko Kimakura et al.: "Toxicity of Topical Antifungal Agents to Stratified Human Cultivated Corneal Epithelial Sheets", JOURNAL OF OCULAR PHARMACOLOGY AND THERAPEUTICS, Vol. 30, No. 10, 1 Dec. 2014, pages 810-814, Kayla R Stover et al.: "Cardiac toxicity of some echinocandin antifungals", EXPERT OPINION ON DRUG SAFETY, Vol. 13, No. 1, 18 Sep. 2013, pages 5-14, Thomas Peter et al.: "Micafungin-Induced Suicidal Erythrocyte Death", CELLULAR PHYSIOLOGY AND BIOCHEMISTRY, Vol. 39, No. 2, 1 Jan. 2016, pages 584-595, Faouzi Saliba et al.: "Randomized Trial of Micafungin for the Prevention of Invasive Fungal Infection in High-Risk Liver Transplant Recipients", CLINICAL INFECTIOUS DISEASES, Vol. 60, No. 7, 17 Dec. 2014, pages 997-1006, J. A. OLSON et al.: "Differences in efficacy and cytokine profiles following echinocandin or liposomal amphotericin B monotherapy or combination therapy for murine pulmonary or systemic *Aspergillus flavus* infections", ANTIMICROBIAL AGENTS AND CHEMOTHERAPY, Vol. 56, No. 1, 3 Oct. 2011, pages 218-230; which all describe the antifungal activities of the echinocandins. Some describe cytotoxic activity of these same echinocandins.

Thus the present invention relates to at least one compound of the echinocandin family, or a pharmaceutical composition comprising at least one compound of the echinocandin family, for use as a cytoprotective drug.

The invention is not intended to treat the extracellular causes of pathological situations or degenerative processes which may lead to cell death, but is indeed for treating the consequences at the cellular level, whether intracellular or membranous, of said pathological situations or degenerative processes and particularly to protect cells against said consequences.

Thus, the invention is not concerned which the antifungal properties of the compounds of the echinocandin family. The invention is concerned with the consequences at the cellular level of said pathological situations or of said degenerative processes, in particular in the absence of infection by fungi, and is particularly directed to protecting cells against said consequences.

Thus to be exact, the present invention relates to at least one compound of the echinocandin family or a pharmaceutical composition comprising at least one compound of the echinocandin family, for use as a cytoprotective drug, it being understood that the present invention excludes any use of said compound of the echinocandin family as an antifungal agent.

More specifically, the invention relates to a compound of the echinocandin family, or a pharmaceutical composition comprising at least one compound of the echinocandin family for use as a drug for the prevention and/or protection and/or treatment of the consequences at the cellular level of the pathological situations or degenerative processes which may lead to cell death, it being understood that said compound of the echinocandin family is not for use as an antifungal agent.

More specifically, the invention relates to a compound of the echinocandin family, or a pharmaceutical composition comprising it, for use as a drug for preventing and/or protecting and/or treating cells against the consequences at the cellular level of pathological situations or degenerative processes which may lead to cell death, it being understood that said compound of the echinocandin family used alone or in said composition is not for use as an antifungal agent.

By "pharmaceutical composition" according to the invention is meant a composition comprising at least one compound of the echinocandin family and of which the other components are pharmaceutically acceptable.

According to the invention, the compound of the echinocandin family may be selected from caspofungin, micafungin, anidulafungin, cilofungin, enfumafungin, arundifungin, echinocandin B, biafungin, CD101 IV or rezafungin, pneumocandins, arbocandins and papulacandins, or one of their semi-synthetic derivatives or one of their salts or one of their esters, or one of their ester salts.

Preferably according to the invention, the compound of the echinocandin family may be selected from caspofungin, micafungin, and anidulafungin, even more preferably the compound of the echinocandin family may be micafungin, or one of its semi-synthetic derivatives or one of their salts or one of their esters, or one of their ester salts.

According to the invention, the compound of the echinocandin family may be used alone or in a mixture with one or more other compounds of the echinocandin family.

The compound of the echinocandin family or any pharmaceutical composition comprising it may be used, for the prevention, advantageously in individuals at risk, and/or for the protection and/or the treatment of human beings and/or animals, particularly mammals, preferably the human being.

Advantageously the compound of the echinocandin family or any pharmaceutical composition comprising it may be used in an organ donor, tissue donor or cell donor, living or clinically dead, an organ recipient, tissue recipient or cell recipient, before, during or after transplant, and/or more specifically an organ, tissue or cells, whether the organ, tissue or cells are in situ, for example in the case of a medical or surgical procedure or during a pathology, but also an organ, tissue or cells ex vivo, for example at the time of certain specific surgeries which may require the temporary removal of an organ, tissue or cells from the body, in particular to modify or purify them, or during transport and preservation of an organ, tissue or cells, during transplant or during reperfusion of the organ, tissue or cells after its or their reimplantation.

This protection may therefore be implemented in a general way to the individual, donor or recipient, or to an organ, tissue or cells in situ or ex vivo, for example during certain surgeries or during its or their transport or its or their preservation for reimplantation.

According to the invention, the salts of addition with pharmaceutically acceptable acids may be, for example, salts formed with hydrochloric, hydrobromic, nitric, sulphuric, phosphoric, benzoic, maleic, fumaric, succinic, tartaric, citric, oxalic, glyoxylic, aspartic, alkanesulphonic acids such as methanesulphonic or ethanesulphonic acids, arylsulphonic acids, such as benzenesulphonic or paratoluenesulphonic acids, or carboxylic acids, such as formic, acetic or propionic acids.

The advantageous cytoprotective properties demonstrated by the applicant of the compounds of the echinocandin family justify their use, alone or in a pharmaceutical composition, as a cytoprotective drug, that is to say for protecting, preventing and/or treating cells against the consequences at the cellular level of pathological situations or degenerative processes and particularly those that can lead to cell death, particularly pathological necrosis and/or pathological apoptosis and/or pyroptosis and/or necroptosis and/or ferroptosis and/or parthanatosis and/or autophagy (antinecrotic and/or antiapoptotic and/or antipyroptotic and/or antipyroptotic and/or antiferroptotic and/or antiparthanatotic and/or antiautophagic drugs), and/or diseases or conditions for example such as
- circulatory diseases,
- kidney diseases,
- cardiovascular diseases,
- neurological diseases,
- muscle diseases,
- organ-specific or systemic inflammatory or autoimmune diseases,
- diseases of bones, joints, connective tissue and cartilage,
- ischemic diseases or attacks of the limbs
- skin diseases,
- hematological and vascular diseases,
- lung diseases,
- diseases of the gastrointestinal tract,
- liver diseases,
- metabolic diseases,
- diseases of the pancreas,
- severe poisoning by chemical agents, infectious agents, toxins or drugs,
- disorders associated with aging,
- dental disorders,
- ophthalmic diseases or disorders,
- diseases of the auditory tract,
- diseases associated with the mitochondria (mitochondrial pathologies), etc., and/or trauma and/or exposure to factors of physical and/or chemical and/or biological origin and/or events such as accidental occlusions and hemorrhages, and/or medical and/or surgical procedures such as cell, tissue or organ transplants.

Advantageously, the compounds of the echinocandin family can be used, alone or in a pharmaceutical composition, for example for the prevention and/or protection and/or treatment of cardiac cells (cardioprotective drug), liver (hepatoprotective drug), kidney (nephroprotective drug), preferably for the protection of kidney cells (nephroprotective drug), very preferably endothelial, podocytic and/or renal epithelial cells, even more preferably renal epithelial cells.

The present invention also relates to at least one compound of the echinocandin family, or a pharmaceutical composition comprising at least one compound of the echinocandin family, as a cytoprotective drug, particularly in the prevention and/or protection and/or treatment of cell death in an organ donor and/or in a recipient of an organ and/or a transplant organ, and/or to prevent acute transplant rejection and/or to increase the long-term survival of an organ, and/or to limit primary non-function of an organ and/or to limit delayed resumption of function of a transplanted organ and/or to improve the functional resumption of a transplant organ, primarily the treatment or the prevention of cell death of a transplant organ.

The phenomenon of ischemia may correspond to a reduction in the blood supply to an organ, linked for example without limitation to a thrombosis, an atheromatous plaque, compression of an artery for example by crushing a limb, by a tourniquet, a hematoma, a tumor, or an effusion of liquid, a voluntary stoppage of blood circulation particularly during operations requiring it, hemorrhage or hypoperfusion preventing certain tissues from being properly nourished, etc. This decrease can lead to a drop in oxygenation of the tissues and cells of the organ below its needs (hypoxia) and the disruption, or even cessation, of its function. Ischemia may be reversible or irreversible, and may then lead to organ infarction, i.e. the death of part or all of the organ or the tissues or cells of which it is composed.

The consequences of these ischemias or hypoperfusions can affect all organs, particularly among others the kidneys, liver, heart, lungs, intestines, brain or a limb.

The damage at the cellular level can be such that it can have dramatic consequences, even jeopardizing the survival of the individual.

Reperfusion occurs when the blood circulation in an organ is restored after a period of ischemia. It is well-established that during reperfusion, the organ undergoes tissue or cellular damage again, which can limit its recovery of function. Here too, the cellular or tissue damage can be such that it can lead to serious consequences that may even jeopardize the survival of the individual.

The phenomenon of ischemia-reperfusion, which will associate both ischemia- and reperfusion-related damage, is a complex issue that may involve several types of cell death and cascades of molecular reactions.

Surprisingly and unexpectedly, the inventors have shown that compounds of the echinocandin family can increase the survival of animals that have undergone ischemic reperfusion of an organ and human or animal cells from different types of organs that have suffered oxygen and nutrient deprivation stress.

Advantageously, the invention addresses the treatment or prevention of cell death, and/or pathological situations or degenerative processes when these are associated with ischemia-reperfusion, particularly those leading to cell death.

By "associated with ischemia-reperfusion" according to the invention is meant that the pathological situation and/or the degenerative process and/or the cell death process is at least partly due to an ischemia-reperfusion phenomenon, whether a phenomenon of actual ischemia, hot or cold, and/or a phenomenon of actual reperfusion, and/or a phenomenon of ischemia reperfusion.

Thus the present invention also relates to at least one compound of the echinocandin family, or a pharmaceutical composition comprising at least one compound of the echinocandin family, for use as a drug in the prevention and/or protection and/or treatment of pathological situations or degenerative processes, particularly those leading to cell death, linked to ischemia-reperfusion conditions, whether a phenomenon of actual ischemia, hot or cold, and/or an actual phenomenon of reperfusion, and/or an ischemia-reperfusion phenomenon.

Another object of the invention concerns at least one compound of the echinocandin family, or a pharmaceutical composition comprising at least one compound of the echinocandin family, intended to be used as a drug for the prevention and/or protection and/or treatment of an organ, a tissue or a cell, against ischemia-reperfusion lesions which may occur during a hot or cold ischemia phenomenon proper, and/or a reperfusion phenomenon proper, and/or an ischemia-reperfusion phenomenon.

In a preferred form, the compound of the echinocandin family, or a pharmaceutical composition comprising at least one compound of the echinocandin family, may be for use as a drug for the prevention and/or protection and/or treatment of heart failure due to an infarction, neurological sequalae due to stroke or trauma, tissue damage affecting the liver, intestine, heart, lung or kidney further to their transplant to a transplant or to surgery, or the consequences of the surgical procedures.

According to an even more preferred form of the invention, the compound of the echinocandin family, or a pharmaceutical composition comprising at least one compound of the echinocandin family, may be for use as a drug for the prevention and/or protection and/or treatment of renal failure due either to a phenomenon of actual ischemia, hot or cold, and/or to a phenomenon of actual reperfusion, and/or a phenomenon of ischemia reperfusion.

According to the invention, the compound of the echinocandin family may advantageously be used alone or in a pharmaceutical composition, in physiologically effective amounts.

As drugs, the compound of the echinocandin family, or said pharmaceutical composition comprising at least one compound of the echinocandin family, may be formulated for the digestive or parenteral tract.

Alone or in the pharmaceutical composition according to the invention, the compound of the echinocandin family may be present in an amount comprised from 0.00001 to 100%, preferably from 1 to 100% and even more preferably from 10 to 100% of the total weight of the drug or the composition.

The pharmaceutical composition according to the invention comprising at least one compound of the echinocandin family, may furthermore comprise at least one other therapeutically active ingredient, whether active on the same pathology or on a different pathology, for use that is simultaneous, separate or spread out over time, in particular in prevention in an individual at risk and/or during a treatment in an individual suffering from at least one of the pathological situations or at least one of the previously mentioned degenerative processes. It is understood that for simultaneous use the compounds present may be, in said pharmaceutical composition comprising them, mixed together or physically separated, and that for use that is separate or spread out over time the compounds present must be physically separate.

The invention therefore also concerns a pharmaceutical composition comprising at least one compound of the echinocandin family as described above, and in addition at least one other therapeutically active ingredient, whether active on the same pathology or on a different pathology.

Other therapeutically active ingredients include hypo-uricemiant compounds.

In the present text, the term "hypo-uricemiant" refers to a compound that decreases the level of uric acid in the blood.

Thus the invention also relates to pharmaceutical composition which may comprise at least one compound of the echinocandin family and at least one hypo-uricemiant compound.

The hypo-uricemiant compound may be any pharmaceutically acceptable hypo-uricemiant compound. According to the invention, the hypo-uricemiant compound may be selected from a xanthine oxidase inhibitor, for example allopurinol, or febuxostat, or from probenecid, benzbromarone, urate oxidase, or a mixture thereof.

Thus the invention also relates to a pharmaceutical composition which may comprise at least one compound of the echinocandin family and at least one hypo-uricemiant compound, preferably selected from a xanthine oxidase inhibitor, for example allopurinol, or febuxostat, or from probenecid, benzbromarone, urate oxidase, or a mixture thereof.

According to the invention, the hypo-uricemiant compound may be used alone or in a mixture with one or more other hypo-uricemiant compounds.

According to the invention, the hypo-uricemiant compound may be in any pharmaceutically acceptable form, for example in the form of a pharmaceutically acceptable salt or complex, in particular in the form of a sodium salt.

Preferably according to the invention, the hypo-uricemiant compound can be a xanthine oxidase inhibitor, advantageously in the form of a sodium salt, preferably allopurinol, advantageously in the form of a sodium salt.

Thus the invention is particularly aimed at a pharmaceutical composition which may comprise at least one compound of the echinocandin family, and at least one xanthine oxidase inhibitor, advantageously in the form of a sodium salt, preferably allopurinol, advantageously in the form of a sodium salt.

In a much preferred form the invention relates to a pharmaceutical composition which may comprise at least micafungin or one of its semi-synthetic derivatives or one of their salts or one of their esters, or one of their ester salts and at least one hypo-uricemiant compound, preferably in the form of a sodium salt, preferably a xanthine oxidase inhibitor, advantageously in the form of a sodium salt, very preferably allopurinol, advantageously in the form of a sodium salt.

The invention also relates to a pharmaceutical composition comprising at least one compound of the echinocandin family, and in addition at least one other therapeutically active ingredient as described above, whether active on the same pathology or on a different pathology, for use that is simultaneous, separate or spread over time, for use as a drug.

Thus the invention also relates to a pharmaceutical composition which may comprise at least one compound of the echinocandin family and at least one hypo-uricemiant compound selected from a xanthine oxidase inhibitor, for example allopurinol, or febuxostat, or from probenecid, benzbromarone, urate oxidase, or a mixture thereof, for use that is simultaneous, separate or spread over time, for use as a drug.

The invention also relates to a pharmaceutical composition which may comprise at least one compound of the echinocandin family and at least one xanthine oxidase inhibitor, advantageously in the form of a sodium salt, preferably allopurinol, advantageously in the form of a sodium salt, for use as a drug.

The invention also relates to a pharmaceutical composition comprising at least one compound of the echinocandin family, and in addition at least one other therapeutically active ingredient as described above, whether active on the same pathology or on a different pathology, for use that is simultaneous, separate or spread over time, for use as a cytoprotective drug or as a drug for treating a subject suffering from one of the above-mentioned pathological situations or degenerative processes.

Thus the invention also relates to a pharmaceutical composition which may comprise at least one compound of the echinocandin family and at least one hypouricemia compound selected from a xanthine oxidase inhibitor, for example allopurinol, or febuxostat, or from probenecid, benzbromarone, urate oxidase, or a mixture thereof for use that is simultaneous, separate or spread over time, for use as a cytoprotective drug or as a drug for use in the prevention and/or protection and/or treatment of the consequences at the cellular level of the aforementioned pathological situations or degenerative processes.

The invention also relates to a pharmaceutical composition which may comprise at least one compound of the echinocandin family and at least one xanthine oxidase inhibitor, advantageously in the form of a sodium salt, preferably allopurinol, advantageously in the form of a sodium salt, for use as a cytoprotective drug or as a drug for use in the prevention and/or protection and/or treatment of the consequences at the cellular level of the aforementioned pathological situations or degenerative processes.

In a much preferred form, the invention concerns a pharmaceutical composition which may comprise at least micafungin or one of its semi-synthetic derivatives or one of their salts or one of their esters, or one of their ester salts and at least one hypo-uricemiant compound, advantageously in the form of a sodium salt, preferably a xanthine oxidase inhibitor, advantageously in the form of a sodium salt, very preferably allopurinol, advantageously in the form of a sodium salt, for use as a cytoprotective drug or as a drug for use in the prevention and/or protection and/or treatment of the consequences at the cellular level of the previously described pathological situations or degenerative processes, and/or for treating a subject suffering from one of the aforementioned pathological situations or degenerative processes.

Unless otherwise indicated, the embodiments and definitions described for the use of echinocandins according to the invention as a cytoprotective drug as well as concerning the administration and dosage are also to be taken into account for this aspect of the invention which concerns the composition.

The invention also concerns a pharmaceutical composition comprising at least one compound of the echinocandin family, and in addition at least one other therapeutically active ingredient as described above, whether it is active on the same or on a different pathology, for use that is simultaneous, separate or spread over time, or at least one hypo-uricemiant compound, preferably selected from a xanthine oxidase inhibitor, for example allopurinol, or febuxostat, or from probenecid, benzbromarone, urate oxidase, or a mixture thereof, or at least one xanthine oxidase inhibitor, advantageously in the form of a sodium salt, preferably allopurinol, advantageously in the form of a sodium salt, for use that is simultaneous, separate or spread over time as a drug for the prevention and/or protection and/or treatment of an organ, of a tissue or cell, against ischemia-reperfusion lesions which may occur during an actual ischemia phenomenon, hot or cold proper, and/or an actual reperfusion phenomenon, and/or an ischemia-reperfusion phenomenon.

In a much preferred form, the invention concerns a pharmaceutical composition which may comprise at least micafungin or one of its semi-synthetic derivatives or one of their salts or one of their esters, or one of their ester salts and at least one hypo-uricemiant compound, advantageously in the form of a sodium salt, preferably a xanthine oxidase inhibitor, advantageously in the form of a sodium salt, very preferably allopurinol, advantageously in the form of a sodium salt, for use as a drug for the prevention and/or protection and/or treatment of an organ, a tissue or a cell, against the ischemia-reperfusion lesions which may occur during an actual ischemia phenomenon, hot or cold, and/or an actual reperfusion phenomenon, and/or an ischemia-reperfusion phenomenon.

According to an embodiment of the invention, when the pharmaceutical composition comprises at least one compound of the echinocandin family as described above and at least one other therapeutically active ingredient as described above, advantageously at least one hypo-uricemiant compound, preferably chosen from a xanthine oxidase inhibitor, for example allopurinol, or febuxostat, or from probenecid, benzbromarone, urate oxidase, or a mixture thereof, or at least one xanthine oxidase inhibitor, advantageously in the form of a sodium salt, preferably allopurinol, the amount of the compound of the echinocandin family may be between about 0.00025 mg and about 400000 mg, preferably between about 50 mg and about 6000 mg, of compound of the echinocandin family per gram of the other therapeutically active compound.

The composition according to the invention may be in different forms for example such as a single composition comprising at least one compound of the echinocandin family and at least one other therapeutically active ingredient as described above, but also in the form of two or more compositions each comprising at least the compound of the echinocandin family and/or at least the other therapeutically active ingredient as described above.

Preferably according to the invention, the composition will be understood to be a single composition comprising at least one compound of the echinocandin family and at least and at least one other therapeutically active ingredient as described above.

According to the invention, the compound of the echinocandin family and/or the other therapeutically active ingredient of the composition may be in a dosage form in common between them. Also according to the invention, the compound of the echinocandin family and the other therapeutically active ingredient of the composition may be in identical or different dosage forms.

It is therefore understood that when, according to the invention, the compound of the echinocandin family and the other therapeutically active ingredient of the composition are in a common dosage form, they may be administered simultaneously, that is to say at the same time, and using the same administration route.

It is also understood that when, according to the invention, the compound of the echinocandin family and the other therapeutically active ingredient of the composition are in identical or different dosage forms, they may be administered either simultaneously, successively or separately, using identical or different administration routes.

Preferably, when the administration is successive, all the compounds of the composition are administered within an interval of not more than about one hour, preferably not more than about 10 minutes, even more preferably not more than about one minute.

When the composition according to the invention comprises more than two therapeutically active compounds, some compounds may be administered simultaneously, some compounds may be administered successively, and/or some compounds may be administered separately.

According to the invention, the compound of the echinocandin family can be used in admixture with one or more acceptable excipients or inert carriers, that is to say pharmaceutically inactive and non-toxic excipients, the purpose of which may be to impart a particular consistency or other particular physical or taste characteristics to the finished product, avoiding any chemical interaction with the therapeutically active compounds. Examples include saline, physiological, isotonic, buffered solutions, etc., compatible with pharmaceutical use and known to the person skilled in the art. The compositions according to the invention can contain one or more agents or vehicles selected from dispersants, solubilizers, stabilizers, preservatives, sweeteners, flavorings, anti-caking agents, lubricants, disintegrants, adsorbents, etc. Agents or vehicles which can be used in formulations (liquid and/or injectable and/or solid) are in particular methylcellulose, hydroxymethylcellulose, carboxymethylcellulose, cyclodextrins, polysorbate 80, mannitol, gelatin, lactose, vegetable or animal oils, etc. Vegetable oils are preferably used. The compounds of the echinocandin family and the pharmaceutical compositions according to the invention can be formulated in the form of a suspension or ready-to-use or extemporaneous injectable solution, gels, oils, tablets, suppositories, powders, capsules, granules, suspensions, emulsions, polymers, nanoparticles, microspheres, rectal capsules, enemas, pastes, ointments, creams, plasters, portions, implants, sprays, aerosols, etc., optionally by means of dosage forms or devices for controlled and/or delayed release. For this type of formulation, an agent such as cellulose, carbonates or starches is advantageously used.

In a particular embodiment, the compound of the echinocandin family or the pharmaceutical composition comprising it can be formulated in the form of a powder to be reconstituted for intravenous injection.

Administration may be by any method known to the skilled person, preferably oral or parenteral, for example by injection, intraperitoneal, intracerebral, intrathecal, intravenous, intra-arterial or intramuscular. Oral or intravenous administration is preferred. For long-term treatment, the preferred administration route is sublingual, oral or transcutaneous.

For injections, the compounds are generally packaged as liquid solutions or suspensions, which can be injected using syringes or infusions, for example. It is understood that the rate and/or amount injected, or generally the amount to be administered, can be adapted by the person skilled in the art according to the individual, the pathology, the mode of administration, etc. It is understood that repeated administrations may be performed, possibly in combination with other active ingredients and/or any pharmaceutically acceptable vehicle (buffers, saline solutions, isotonic solutions, in the presence of stabilizing agents, etc.).

According to certain aspects, the compound or pharmaceutical composition according to the invention can be administered before, during or after the occurrence of the process that can lead to cell death, for example before a surgical procedure such as angioplasty, or during an operation requiring the bypassing of the heart, or when an individual is at risk of being a victim of an ischemic event such as cardiac or cardiovascular ischemia. According to certain aspects, the compound or pharmaceutical composition according to the invention can be administered after the occurrence of the process that can lead to cell death, such as after an infarction, etc.

Where the pathological situation and/or the degenerative process and/or the cell death process is at least partly due to an ischemia-reperfusion phenomenon, the pharmaceutical compound or composition according to the invention can be administered before the ischemia, and/or during the ischemia, and/or after the ischemia, and/or before the reperfusion, and/or during the reperfusion, and/or after the reperfusion.

The bringing into contact of an organ, whether the organ is in situ or ex vivo, with the compound or composition according to the invention may be carried out by any known means, for example by direct contact on the organ by sprinkling, perfusion, immersion, dipping, flushing, etc.

In general, the daily dose of a compound will be the minimum dose to achieve the desired therapeutic effect. The doses of the compounds of the echinocandin family described above may generally be comprised between 0.01 and 150 mg per kilo per day for a human being, preferably between 0.1 and 50 mg per kilo per day for a human being, even more preferably between 0.2 and 40 mg per kilo per day for a human being, very preferably between 0.25 and 30 mg per kilo per day for a human being, extremely preferably between 4 and 30 mg per kilo per day for a human being.

The doses of hypo-uricemiant compounds can generally be between 0.1 and 150 mg per kilogram per day for a human being, preferably between 1 and 10 mg per kilogram per day for a human being, or even more preferably between 3 and 5 mg per kilogram per day for a human being.

If necessary, the daily amount may be administered in one, two, three, four, five, six or more doses taken per day or in multiple sub-quantities administered at appropriate intervals during the day.

The amount chosen may depend on multiple factors, in particular the administration route, the duration of administration, the at which administration is carried out, the rate of elimination of the compound, the different product(s) used in combination with the compound or composition, the age, weight and physical condition of the individual, as well as the individual's medical history, the nature of his or her pathological situation or the degenerative process he or she is facing, and any other information known in medicine.

The doctor's prescription may start at lower amounts than those generally used, then these amounts will be gradually increased to better control the appearance of possible side effects.

Preferably the compound or composition according to the invention may be administered for a period ranging from 1 day to 5 weeks, even more preferably for a period ranging from 1 day to 1 week.

The present invention also relates to a method of treatment which can include administering a therapeutically effective amount of a compound of the echinocandin family or a composition according to the invention to a human or animal in need thereof.

The present invention also relates to a process for the preparation of a pharmaceutical composition comprising a compound of the echinocandin family according to the above described invention, characterized in that the compounds of the composition according to the invention are mixed, according to methods known per se, with acceptable excipients, in particular pharmaceutically acceptable excipients.

The invention also relates to the use of at least one compound of the echinocandin family or of a composition comprising it according to the invention, for the preparation of an organ preservation solution.

Such an organ preservation solution comprising at least one compound of the echinocandin family can be prepared for example from any existing organ preservation solution for example such as any solution for infusion, storage, transport and/or rinsing of an organ. Such solutions can be, for example, Belzer UW® cold preservation solution, Custodiol®, Celsior®, IGL1e, Scot 15® preservation solution, Viaspan®, RENOGRAF®, or a mixture of these.

The invention also relates to a solution which may comprise at least one compound of the echinocandin family or a pharmaceutical composition comprising it, intended for organ preservation (preservation solution).

A preservation solution according to the invention may be used for example for infusing an organ in situ before removal from a donor, and optionally cooling it, and/or for rinsing and/or storing and/or transporting an organ after removal, for example statically, or by infusing it for example in an infusion machine, whether with or without oxygen supply, and at different temperatures ranging from hypothermia to normothermia.

According to the invention, said preservation solution may contain at least one compound of the echinocandin family or a drug or composition comprising it according to the invention in an amount sufficient to prevent/mitigate/limit lesions due to processes which can lead to cell death, particularly lesions due to ischemia-reperfusion.

For example, the compound of the echinocandin family, used alone or in a pharmaceutical composition containing it, may be present in the preservative solution at a concentration of from 0.1 to 150 mg/L, preferably from 1 to 50 mg/L and even more preferably from 10 to 40 mg/L of preservative solution. Advantageously, the organ preservation solution according to the invention may be used for infusing and/or storing and/or transporting or rinsing an organ for example such as the liver, lung, heart, kidney, or pancreas, preferentially the kidney.

The compound of the echinocandin family or the composition comprising it according to the invention may be added to an organ preservation solution for a few hours to a few minutes before use of the solution for infusing and/or storing and/or transporting and/or rinsing the organ.

It may also be envisioned that the compound of the echinocandin family, or the composition comprising it, can be added when the organ may already be present in the preservative solution. For example, the echinocandin compound or the composition comprising it may be added to the preservation solution at any time during hot ischemia, cold ischemia, or reperfusion.

The hypo-uricemiant compound may be present in the preservative solution at a concentration of from 0.1 to 150 mg/L, preferably 1 to 50 mg/L and even more preferably 1 to 10 mg/L of preservative solution.

When, according to the invention, the compound of the echinocandin family and the hypo-uricemiant compound of the composition are in a common dosage form, they may be added simultaneously to the preservative solution. When, according to the invention, the compound of the echinocandin family and the hypo-uricemiant compound of the composition are in identical or different dosage forms, they may be added to the preservative solution either simultaneously or successively.

Another object of the invention relates to a process for extemporaneously preparing an organ preservation solution comprising at least one compound of the echinocandin family, which comprises a step of mixing at least one organ preservation solution with at least one compound of the echinocandin family. According to the invention, when at least one compound of the echinocandin family is used for the preparation of a transplant organ preservation solution, the mixture may be formulated so as to be compatible with such use.

The present invention also relates to a method for the prevention and/or protection and/or treatment of an organ, tissue or cell against ischemia-reperfusion lesions which may occur during a actual hot or cold ischemia phenomenon and/or an actual reperfusion phenomenon, and/or an ischemia-reperfusion phenomenon, which comprises bringing said organ, tissue or cell into contact with at least one compound of the echinocandin family, or a drug or composition according to the invention or at least one organ preservation solution according to the invention.

Another object of the invention relates to the use of a compound of the echinocandin family, of a drug, of a composition according to the invention or of a preservative solution according to the invention, for the prevention and/or protection and/or treatment of an organ, tissue or cell against ischemia-reperfusion lesions which may occur during a phenomenon of actual ischemia, hot or cold, and/or a phenomenon of actual reperfusion, and/or a phenomenon of ischemia-reperfusion.

Another object of the invention relates to the use of a compound of the echinocandin family, a drug, a composition or a preservation solution according to the invention, for the prevention and/or protection and/or treatment of an organ, tissue or cell, against lesions that may occur during ischemia-reperfusion phenomena.

Since an object of the invention can concern a pharmaceutical composition which may contain a combination of therapeutically active compounds which can be co-administered separately, the invention also relates to a kit comprising at least one compound of the echinocandin family, or one of its semi-synthetic derivatives or one of their salts or one of their esters, or one of their ester salts, and at least one other therapeutically active ingredient as described above, whether it is active on the same pathology or on a different pathology, preferably a hypo-uricemiant compound or one of its salts as defined above.

The kit according to the invention may comprise a container for receiving a compound of the echinocandin family and another therapeutically active ingredient separately, or each compartment may comprise one or more amounts comprising the compound of the echinocandin family or the other therapeutically active ingredient. Alternatively, the kit may comprise separate compartments, wherein each compartment may comprise one or more amounts of compound of the echinocandin family and one or more amounts of the other therapeutically active ingredient.

The kit may include an instructions for use.

The kit is particularly advantageous, for example, when the separate components are administered in different amounts, by different routes (oral, parenteral), at different intervals, or when the patient or health care professional has to measure a desired amount of each of the components: composed of the echinocandin family and other therapeutically active ingredient.

The kit may also be advantageous, for example, when separate components are added successively or simultaneously to an organ preservation solution.

Figure 1A:
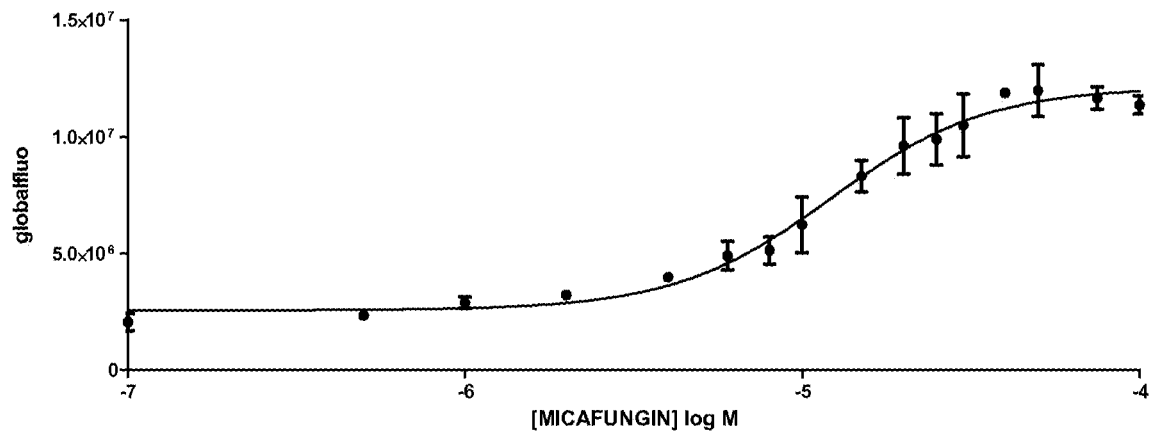
FIG. 1A and FIG. 1B represents the effects of micafungin and anidulafungin on the survival of human kidney glomerular endothelial cells in an in vitro model of oxygen and nutrient deprivation.

Other advantages and particularities of the invention may appear in the following examples.

I) Effect of the compounds on cell survival.

Protocol

To demonstrate the cytoprotective action of echinocandins, the applicant studied their activities on different human and animal primary cell types in an in vitro model of oxygen and glucose deprivation followed by oxygen and glucose replenishment.

Anidulafungin and micafungin were tested on Human Renal Glomerular Endothelial Cells (HRGEC, Innoprot P10665), on Human Renal Proximal Tubular Epithelial Cells (HRPTEpiC, Innoprot P10662), on Human Astrocytes (HA, caltag SC-1800), on Human Cardiac Microvascular Endothelial Cells (HCMEC, Caltag SC-6000), on Human Hepatic Sinusoidal Endothelial Cells (HHSEC, Caltag SC-5000), on Rat Primary Kidney Glomerular Endothelial cells (Cellbiologics, RN-6014G) and on Bovine Brain Microvascular Endothelial Cells (BBMEC, Caltag SC-B100).

In a first phase, these isolated, purified and cryopreserved cells are thawed and multiplied according to the supplier's recommendations in T75 or T175 flasks pre-coated with 2 µg of fibronectin/claim$^2$ (CORNING) for HRGEC, HCMEC, HHSEC and BBMEC, or 2 µg poly-L-lysin/cm$^2$ (Caltag SC-0403) for HRPTEpiC and HA, or 15 mL/flask 175 cm$^2$ gelatin-based solution (Cellbiologics) in the presence of endothelial cell supplemented growth medium ECM (P60104, INNOPROT, Caltag, SC-1001) for HRGEC, HCMEC, HHSEC, RPKGEC or BBMEC, or astrocyte cell supplemented growth medium AM (Caltag SC-1801) for HA or epithelial cell supplemented growth medium EpiCM (P60106, INNOPROT) for HRPTEpiC, at 37° C. under 5% $CO_2$ and saturated humidity until their confluency. They are then harvested by trypsinization according to the method described by the supplier for exactly 5 minutes and then reseeded in new flasks a maximum of three times.

To carry out the oxygen and glucose deprivation test followed by their replenishment, the cells will be seeded in 96-well black plates with transparent flat bottom (GREINER). Once a sufficient number of cells has been obtained to allow seeding of 2000 to 15000 cells per well of 96-well plates depending on the cell type, the cells are seeded in these 96-well plates previously coated with an extracellular matrix as listed above for the flasks. The cells are cultured for 5 to 8 days according to the cell type, in the presence of the same growth medium as in the flask as described above except for HRGEC and HRPTEpiC for which DMEM (DUTSCHER) with 1 g/L of supplemented glucose is used, at 37° C. under 5% $CO_2$ and saturated humidity to obtain confluency.

On the first day of oxygen and glucose deprivation, (5th, 6th, 7th or 8th day of culture), the culture conditions are drastically changed. The medium of all plates is removed and replaced by DMEM (DUTSCHER) medium without glucose and supplemented only with 1% penicillin-streptomycin (DUTSCHER). Anidulafungin or micafungin dissolved in dimethyl sulfoxide (DMSO) is then added to each well at the desired concentration, resulting in a maximum of 1% DMSO, and the plates are placed under hypoxia at <1% $O_2$ and 5% $CO_2$ at 37° C. for 24 hours of culture. Each compound was tested in a concentration range.

After 24 hours, the growth medium is changed and replaced by a richer medium, DMEM (DUTSCHER) at 1 g/L glucose and 2% FBS (INNOPROT) and 1% penicillin-streptomycin (DUTSCHER). These media will have been pre-equilibrated at 37° C. in advance. The cells are then returned to culture at 37° C. under 20% $O_2$ and 5% $CO_2$ for 22h.

After 22 hours of reoxygenation, the potential protective effect of anidulafungin or micafungin is measured by a cell viability test using calcein AM (CORNING), which is a dye substrate. The calcein AM can easily cross the cell membrane of the viable cells. The AM ester groups mask the part of the molecule that chelates calcium. Once inside the cells, the (non-fluorescent) calcein AM is hydrolyzed to (fluorescent) calcein by endogenous esterases. The resulting calcein molecule binds to calcium inside the cell and remains trapped inside the cell. These molecules emit strong green fluorescence when subjected to emission of a particular wavelength (495 nm). Since dead cells lack esterase activity, only living cells are labelled.

This cell viability test is performed in two steps. After the 22h reoxygenation, 12 µL of calcein AM previously diluted in PBS (1:24) is added to each well and the cells are incubated at 37° C. under 5% $CO_2$ for 45 min. Next, 15 µL hemoglobin (0.1 g/mL solution in PBS, SIGMA) is added to each well and the cells are returned to 37° C. and 5% $CO_2$ for 15 min. The 96-well plates are lastly read on the plate reader, Plate RUNNER HD(R) marketed by Dioscure, Marseille France, which allows measurement of the fluorescence of surviving adherent cells present in each well (globalfluo in arbitrary units), and to perform multiple image acquisitions in a very short time.

The use of positive control (culture of cells under the same conditions of oxygen deprivation but in the presence of glucose) and negative control (culture of cells under the same conditions of oxygen and glucose deprivation but without the addition of compounds of the echinocandin family) makes it possible to establish a relative scale of effectiveness. Cell protection of 0% corresponds to the mean value of the negative control. This value will be subtracted from all other values used. The 100% cell protection corresponds to the mean value of the positive control minus the mean value of the negative control. This scale is used as a reference to measure the effectiveness of anidulafungin or micafungin cytoprotection relative to the controls in each experiment. For each compound tested, the percentage of cell survival is calculated after subtracting from it the mean value of the negative control relative to the mean value of the positive controls from which has been subtracted in advance the mean value of the negative control.

For each cell type, the means and standard deviation of the raw fluorescence intensity results (globalfluo in arbitrary units) of a minimum of three assays are shown in FIGS. 1 to 7 as a function of the log of the concentration of compound of the echinocandin family used. The dose effect curve is least-squares fitted using GraphPad Prism V5.02 software. The expression of these results in terms of percentage of cell survival is shown in the table included with each example.

EXAMPLE 1: EFFECT OF MICAFUNGIN AND ANIDULAFUNGIN ON THE SURVIVAL OF HUMAN KIDNEY GLOMERULAR ENDOTHELIAL CELLS IN AN IN VITRO MODEL OF OXYGEN AND NUTRIENT DEPRIVATION

| | Globalfluo assay 1 | Globalfluo assay 2 | Globalfluo assay 3 | Mean globalfluo | Survival rate (%) |
|---|---|---|---|---|---|
| [Micafungin] log μM | | | | | |
| −4 | 11181240 | 11805530 | 11095570 | 11360780 | 37 |
| −4.124939 | 12113050 | 11168770 | 11691720 | 11657847 | 38 |
| −4.30103 | 10705920 | 12585990 | 12661760 | 11984557 | 40 |
| −4.39794 | 12034270 | 11904770 | 11704580 | 11881207 | 39 |
| −4.522879 | 9416001 | 11987430 | 10070420 | 10491284 | 34 |
| −4.60206 | 10458840 | 10594720 | 8636463 | 9896674 | 31 |
| −4.69897 | 8790971 | 10993750 | 9050581 | 9611767 | 30 |
| −4.823909 | 9039973 | 8208392 | 7686254 | 8311540 | 25 |
| −5 | 5367938 | 7594623 | 5742300 | 6234954 | 16 |
| −5.09691 | 5198634 | 5680528 | 4518691 | 5132618 | 11 |
| −5.221849 | 5545222 | 4844574 | 4333143 | 4907646 | 10 |
| −5.39794 | 3889914 | 3964004 | 4064339 | 3972752 | 7 |
| −5.69897 | 3399775 | 3118863 | 3166056 | 3228231 | 4 |
| −6 | 3157528 | 2851345 | 2667237 | 2892037 | 2 |
| −6.30103 | 2192241 | 2496288 | 2306718 | 2331749 | 0 |
| −7 | 2276775 | 2276419 | 1622516 | 2058570 | −1 |
| Positive control = 100% survival | 27369665 | 26325970 | 25792680 | 26496105 | 100 |
| Negative control = 0% survival | 2274277 | 2405536 | 2468446 | 2382753 | 0 |
| [Anidulafungin] log μM | | | | | |
| 1.30103 | 10143140 | 10354290 | 10227990 | 10241807 | 27 |
| 1.255273 | 10855790 | 12347330 | 7837444 | 10346855 | 27 |
| 1.20412 | 12170420 | 9545764 | 9735499 | 10483894 | 28 |
| 1.079181 | 12175690 | 10104310 | 9396440 | 10558813 | 28 |
| 1 | 8082278 | 8981812 | 10460790 | 9174960 | 23 |
| 0.90309 | 7152564 | 8021501 | 6792572 | 7322212 | 15 |
| 0.7781513 | 1844220 | 8446890 | 6499110 | 5596740 | 8 |
| 0.60206 | 6404501 | 5391467 | 4055726 | 5283898 | 7 |
| 0.30103 | 3108717 | 8079028 | 4587276 | 5258340 | 7 |
| 0 | 1595273 | 2299957 | 2320330 | 2071853 | −6 |
| Positive control = 100% survival | 29653885 | 27423425 | 28238954 | 28438755 | 100 |
| Negative control = 0% survival | 3639188 | 3454582 | 3450953 | 3514908 | 0 |

Figure 1B:
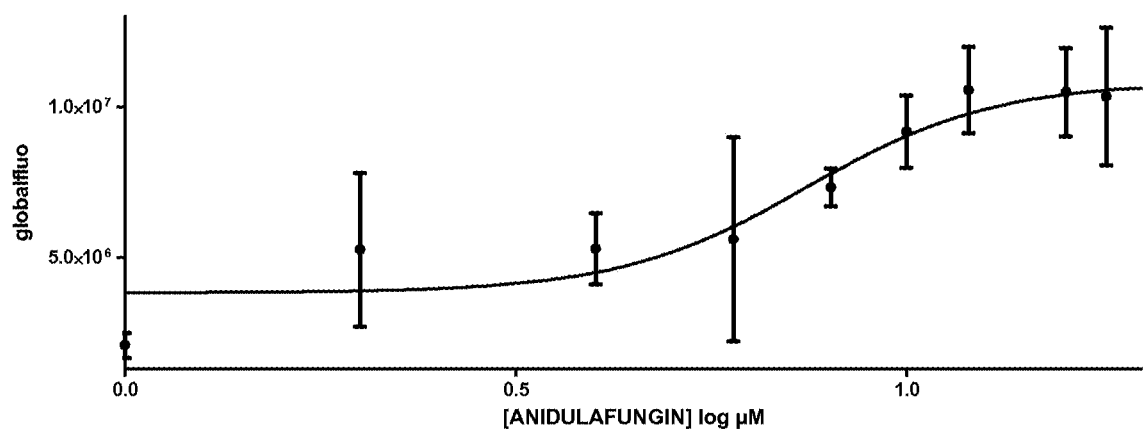

These results are presented graphically in FIGS. 1A and 1B: Micafungin=FIG. 1A; Anidulafungin=FIG. 1B.

Conclusion:

Due to their protective effect against oxygen and nutrient deprivation stress on human renal glomerular endothelial cells, the anidulafungin and the micafungin according to the invention are thus shown to be useful as cytoprotective agents, in particular in the protection of renal cells against deprivation of oxygen and nutrients, and especially in protection against ischemia reperfusion processes.

EXAMPLE 2: EFFECT OF MICAFUNGIN ON THE SURVIVAL OF HUMAN RENAL PROXIMAL TUBULAR EPITHELIAL CELLS IN AN IN VITRO MODEL OF OXYGEN AND NUTRIENT DEPRIVATION

| [Micafungin] log μM | Globalfluo assay 1 | Globalfluo assay 2 | Globalfluo assay 3 | Mean globalfluo | Survival rate (%) |
|---|---|---|---|---|---|
| −4.39794 | 17038910 | 16914110 | 17516930 | 17156650 | 58 |
| −4.69897 | 18487560 | 18879740 | 18282240 | 18549847 | 63 |
| −4.79588 | 17777390 | 17681470 | 18724080 | 18060980 | 61 |
| −4.853872 | 17634840 | 17920170 | 19831830 | 18462280 | 63 |
| −4.920819 | 18495680 | 17954570 | 19304800 | 18585017 | 64 |
| −5 | 19091330 | 21245570 | 20574080 | 20303660 | 71 |
| −5.30103 | 17265090 | 20693980 | 20348120 | 19435730 | 67 |
| −5.69897 | 5296218 | 13559640 | 14370600 | 11075486 | 32 |
| −5.823909 | 4696579 | 8382404 | 9632039 | 7570341 | 18 |
| −6 | 5307945 | 5614600 | 8026091 | 6316212 | 13 |
| −6.09691 | 6028392 | 5998920 | 5793032 | 5940115 | 11 |
| −6.221849 | 4745212 | 4694631 | 5790310 | 5076718 | 8 |
| −6.39794 | 4361975 | 4442347 | 5176795 | 4660372 | 6 |
| −6.69897 | 4839699 | 4005588 | 4289833 | 4378373 | 5 |
| −7 | 3602590 | 3530551 | 3665638 | 3599593 | 2 |
| −8 | 3781795 | 3409519 | 3718559 | 3636624 | 2 |
| Positive control = 100% survival | 26731110 | 28008220 | 27369775 | 27369702 | 100 |
| Negative control = 0% survival | 3103678 | 3369870 | 3236774 | 3236774 | 0 |

Figure 2:
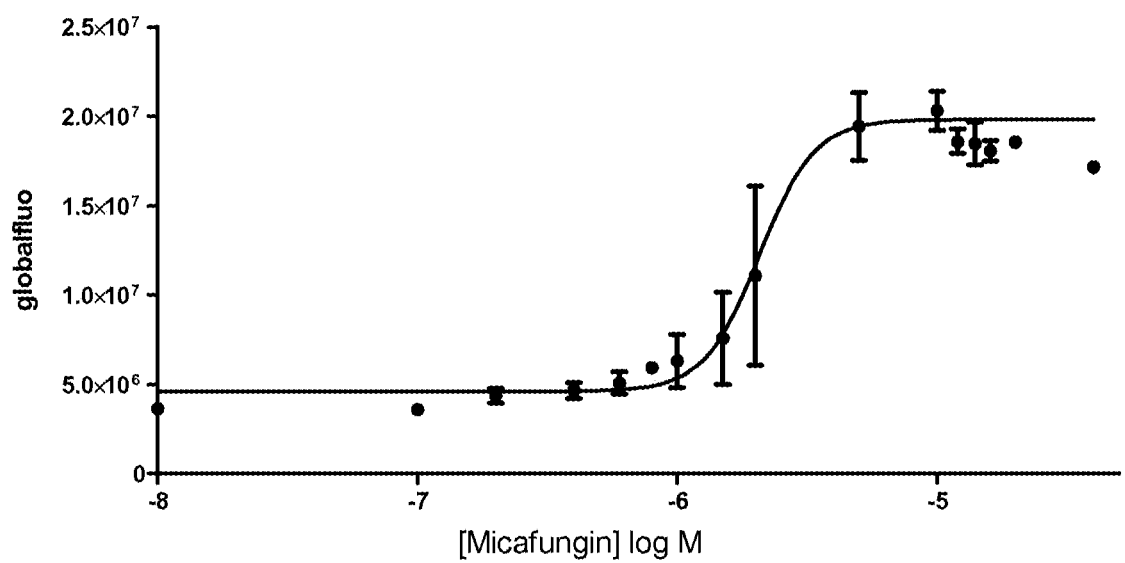
FIG. 2 represents the effects of micafungin on the survival of human renal tubular proximal epithelial cells in an in vitro model of oxygen and nutrient deprivation.

These results are presented graphically in FIG. 2.

Conclusion:

Due to its protective effect against oxygen and nutrient deprivation stress on human renal proximal tubular epithelial cells, micafungin according to the invention is thus shown to be useful as a cytoprotective agent, in particular in the protection of renal cells against oxygen and nutrient deprivation, and especially in protection against ischemia reperfusion processes.

EXAMPLE 3: EFFECT OF MICAFUNGIN AND ANIDULAFUNGIN ON THE SURVIVAL OF HUMAN ASTROCYTE CELLS IN AN IN VITRO MODEL OF OXYGEN AND NUTRIENT DEPRIVATION

| | Globalfluo assay 1 | Globalfluo assay 2 | Globalfluo assay 3 | Mean globalfluo | Survival rate (%) |
|---|---|---|---|---|---|
| [Micafungin] log μM | | | | | |
| 1.477121 | 14577460 | 14402140 | 13825080 | 14268227 | 24 |
| 1.30103 | 11900350 | 13780590 | 15553770 | 13744903 | 21 |
| 1.176091 | 15116230 | 14430130 | 15740520 | 15095627 | 28 |
| 1.079181 | 12974980 | 13357070 | 13693180 | 13341743 | 18 |
| 1 | 15956640 | 14291510 | 16904820 | 15717657 | 32 |
| 0.90309 | 12128260 | 10787240 | 13139350 | 12018283 | 11 |
| 0.7781513 | 12145620 | 12627660 | 12964960 | 12579413 | 14 |
| 0.4771213 | 10184240 | 11122790 | 12211830 | 11172953 | 6 |
| 0 | 11119980 | 10122420 | 9942897 | 10395099 | 2 |
| −0.5228788 | 9708125 | 10748420 | 10103750 | 10186765 | 1 |
| −1 | 12091240 | 10337500 | 9946542 | 10791761 | 4 |
| −2 | 9536623 | 9993250 | 10712930 | 10080934 | 0 |

-continued

| | Globalfluo assay 1 | Globalfluo assay 2 | Globalfluo assay 3 | Mean globalfluo | Survival rate (%) |
|---|---|---|---|---|---|
| Positive control = 100% survival | 27864300 | 27887600 | 28505955 | 28085952 | 100 |
| Negative control = 0% survival | 9686774 | 9906029 | 10453234 | 10015346 | 0 |
| [Anidulafungin] log μM | | | | | |
| 0.90309 | 13394210 | 14898570 | 14923380 | 14405387 | 24 |
| 0.7781513 | 14108250 | 14242150 | 13880120 | 14076840 | 22 |
| 0.60206 | 12006890 | 13270810 | 14798310 | 13358670 | 18 |
| 0.30103 | 13177930 | 13103050 | 13640130 | 13307037 | 18 |
| 0.1760913 | 11838960 | 12087610 | 13326480 | 12417683 | 13 |
| 0 | 11468420 | 12221770 | 14645590 | 12778593 | 15 |
| −0.1249387 | 9674527 | 11462560 | 11240740 | 10792609 | 4 |
| −0.30103 | 12822290 | 11197900 | 11873360 | 11964517 | 10 |
| −0.5228788 | 11050980 | 10353030 | 11612880 | 11005630 | 5 |
| −1 | 9709693 | 10543570 | 12170290 | 10807851 | 4 |
| −2 | 10301450 | 9760112 | 11132460 | 10398007 | 2 |
| Positive control = 100% survival | 28267500 | 29508570 | 27540590 | 28438887 | 100 |
| Negative control = 0% survival | 10180420 | 10441330 | 9486308 | 10036019 | 0 |

Figure 3A:
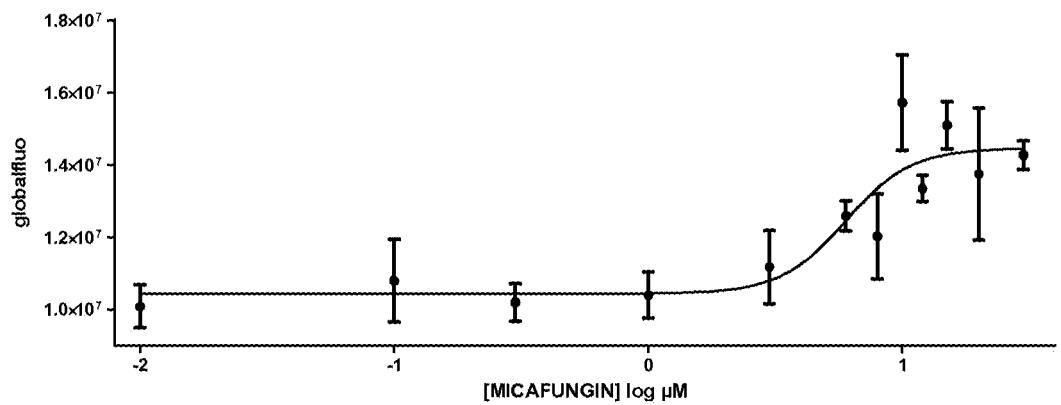
FIG. 3A and FIG. 3B shows the effects of micafungin and anidulafungin on the survival of human astrocyte cells in an in vitro model of oxygen and nutrient deprivation.
Figure 3B:
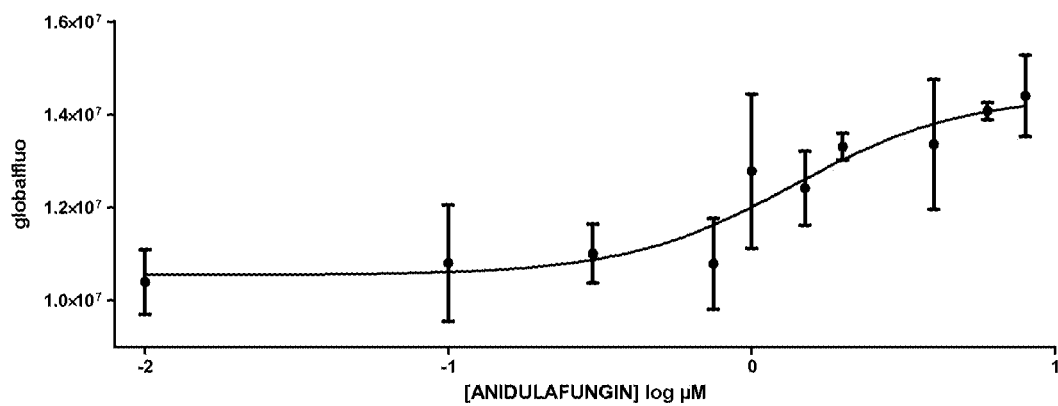

These results are presented graphically in FIGS. 3A and 3B; Micafungin=FIG. 3A; Anidulafungin=FIG. 3B.

Conclusion:

Due to their protective effect against the oxygen and nutrient deprivation stress on human astrocyte cells, the anidulafungin and the micafungin according to the invention are thus shown to be useful as cytoprotective agents, in particular in the protection of brain cells against oxygen and nutrient deprivation, and especially in protection against ischemia reperfusion processes.

EXAMPLE 4: EFFECT OF MICAFUNGIN ON THE SURVIVAL OF HUMAN CARDIAC MICROVASCULAR ENDOTHELIAL CELLS IN AN IN VITRO MODEL OF OXYGEN AND NUTRIENT DEPRIVATION

| [Micafungin] log μM | Globalfluo assay 1 | Globalfluo assay 2 | Globalfluo assay 3 | Mean globalfluo | Survival rate (%) |
|---|---|---|---|---|---|
| 1.477121 | 5692141 | 6434487 | 7272557 | 6466395 | 8 |
| 1.30103 | 6537106 | 5661218 | 6414894 | 6204406 | 7 |
| 1.176091 | 5886475 | 5800515 | 6203727 | 5963572 | 5 |
| 1.079181 | 5365305 | 5914359 | 4948085 | 5409250 | 2 |
| 1 | 5522064 | 5305822 | 6090892 | 5639593 | 3 |
| 0.90309 | 5299685 | 5787047 | 5397439 | 5494724 | 3 |
| 0.7781513 | 5452718 | 4992821 | 6254079 | 5566539 | 3 |
| 0.4771213 | 5103911 | 5348145 | 4886218 | 5112758 | 0 |
| 0 | 4455401 | 4660836 | 4639734 | 4585324 | −3 |
| −0.5228788 | 4445501 | 5528681 | 4443191 | 4805791 | −1 |
| −1 | 4527783 | 4062591 | 5413646 | 4668007 | −2 |
| −2 | 4648220 | 3959524 | 4368024 | 4325256 | −4 |
| Positive control = 100% survival | 22376705 | 22622255 | 22298875 | 22432612 | 100 |
| Negative control = 0% survival | 5292960 | 4873360 | 5006827 | 5057715 | 0 |

Figure 4:
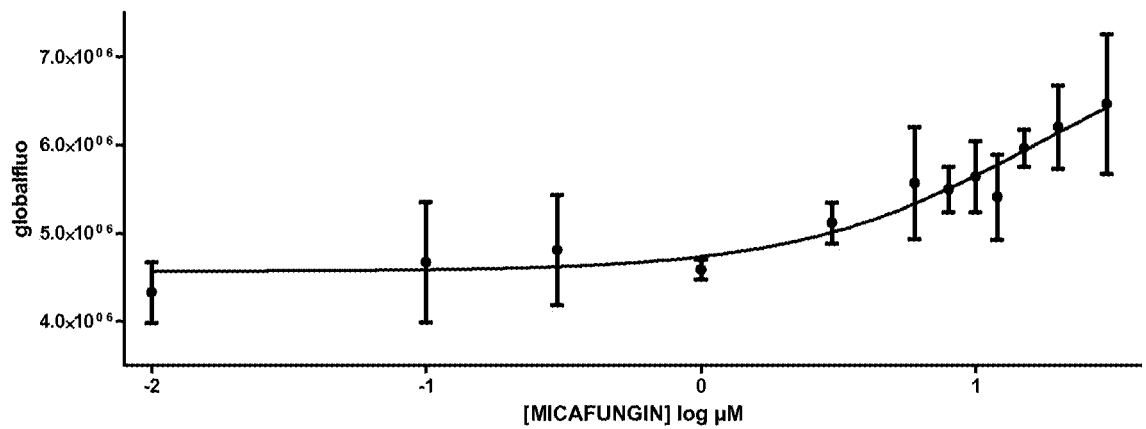
FIG. 4 represents the effects of micafungin on the survival of human cardiac microvascular endothelial cells in an in vitro model of oxygen and nutrient deprivation.

These results are presented graphically in FIG. 4.

Conclusion:

Due to its protective effect against oxygen and nutrient deprivation stress on human cardiac microvascular endothelial cells, micafungin according to the invention is thus shown to be useful as a cytoprotective agent, in particular in the protection of heart cells against oxygen and nutrient deprivation, and especially in protection against ischemia reperfusion processes.

EXAMPLE 5: EFFECT OF MICAFUNGIN ON THE SURVIVAL OF HUMAN HEPATIC SINUSOIDAL ENDOTHELIAL CELLS IN AN IN VITRO MODEL OF OXYGEN AND NUTRIENT DEPRIVATION

| [Micafungin] log μM | Globalfluo assay 1 | Globalfluo assay 2 | Globalfluo assay 3 | Mean globalfluo | Survival rate (%) |
|---|---|---|---|---|---|
| 1.30103 | 3383992 | 2974781 | 3188414 | 3182396 | 3 |
| 1.176091 | 3454603 | 3676802 | 3618017 | 3583141 | 6 |
| 1.079181 | 3383806 | 3457745 | 3493598 | 3445050 | 5 |
| 1 | 3210890 | 3369543 | 2819931 | 3133455 | 3 |
| 0.90309 | 2800146 | 3162662 | 3203256 | 3055355 | 3 |
| 0.7781513 | 2942319 | 3052699 | 2975927 | 2990315 | 2 |
| 0.4771213 | 2619032 | 2696453 | 2858592 | 2724692 | 1 |
| 0 | 2600496 | 2592730 | 2666315 | 2619847 | 0 |
| −2 | 2651037 | 2880244 | 2908835 | 2813372 | 1 |
| 0 | 3063920 | 2647280 | 2608353 | 2773184 | 1 |
| Positive control = 100% survival | 19990125 | 19366245 | 19560320 | 19638897 | 100 |
| Negative control = 0% survival | 2522054 | 2595531 | 2718096 | 2611894 | 0 |

Figure 5:
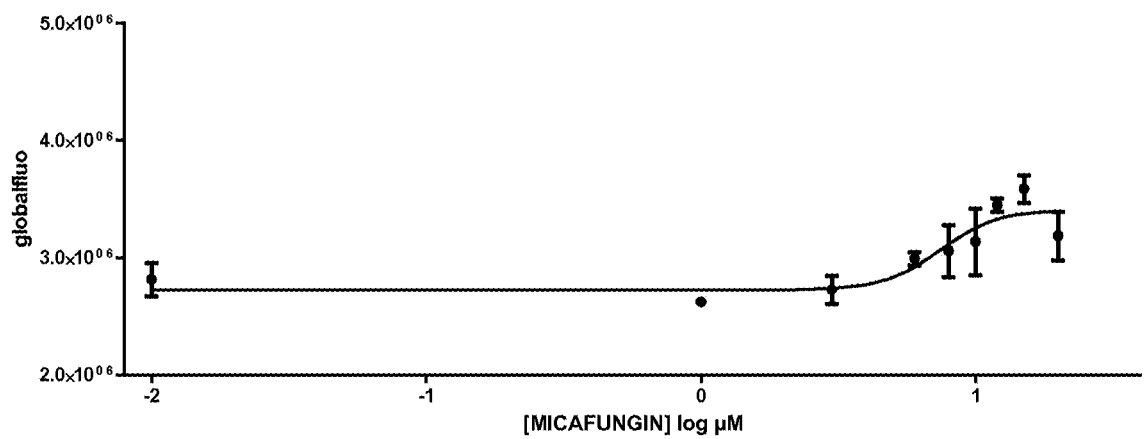
FIG. 5 represents the effects of micafungin on the survival of human liver sinusoidal endothelial cells in an in vitro model of oxygen and nutrient deprivation.

These results are presented graphically in FIG. 5.

Conclusion:

Due to its protective effect against oxygen and nutrient deprivation stress on human liver endothelial cells, micafungin according to the invention is thus shown to be useful as a cytoprotective agent, in particular in the protection of liver cells against oxygen and nutrient deprivation, and especially in protection against ischemia reperfusion processes.

EXAMPLE 6: EFFECT OF MICAFUNGIN AND ANIDULAFUNGIN ON THE SURVIVAL OF RAT KIDNEY GLOMERULAR ENDOTHELIAL CELLS IN AN IN VITRO MODEL OF OXYGEN AND NUTRIENT DEPRIVATION

| | Globalfluo assay 1 | Globalfluo assay 2 | Globalfluo assay 3 | Mean globalfluo | Survival rate (%) |
|---|---|---|---|---|---|
| [Micafungin] log μM | | | | | |
| 2.176091 | 20166170 | 24333680 | 26066530 | 23522127 | 79 |
| 2 | 23318050 | 20442770 | 22906760 | 22222527 | 74 |
| 1.90309 | 25482590 | 16667370 | 22222960 | 21457640 | 71 |
| 1.778151 | 22384980 | 24586670 | 22823930 | 23265193 | 78 |
| 1.60206 | 21279700 | 21255650 | 20543100 | 21026150 | 69 |
| 1.477121 | 23916400 | 22885210 | 21104460 | 22635357 | 75 |
| 1.30103 | 21761030 | 21216730 | 18246850 | 20408203 | 66 |

-continued

| | Globalfluo assay 1 | Globalfluo assay 2 | Globalfluo assay 3 | Mean globalfluo | Survival rate (%) |
|---|---|---|---|---|---|
| 1.176091 | 17307060 | 19173810 | 18057880 | 18179583 | 57 |
| 1.079181 | 11147190 | 19591720 | 15002320 | 15247077 | 46 |
| 1.041393 | 8422700 | 12678250 | 11578770 | 10893240 | 28 |
| 1 | 24112850 | 13345620 | 20572260 | 19343577 | 62 |
| 0.9542425 | 17001920 | 15398170 | 11994410 | 14798167 | 44 |
| 0.90309 | 16467230 | 5461253 | 9297072 | 10408518 | 26 |
| 0.845098 | 7968558 | 13328410 | 4864200 | 8720389 | 19 |
| 0.7781513 | 5553126 | 6638483 | 7505823 | 6565811 | 11 |
| 0.69897 | 14177330 | 11602990 | 9423392 | 11734571 | 31 |
| 0.60206 | 12878800 | 13369330 | 12813230 | 13020453 | 37 |
| 0.4771213 | 4782175 | 7854686 | 4782283 | 5806381 | 8 |
| 0.39794 | 5495171 | 5446233 | 3835973 | 4925792 | 4 |
| 0.30103 | 3351615 | 4221516 | 4567106 | 4046746 | 0 |
| 0.1760913 | 8740776 | 7981119 | 5239211 | 7320369 | 14 |
| 0 | 5417339 | 3464807 | 4867657 | 4583268 | 3 |
| −0.154902 | 3831476 | 4395798 | 3538568 | 3921947 | 0 |
| −0.30103 | 4962690 | 4263110 | 4133198 | 4452999 | 2 |
| −0.5228788 | 4164368 | 5246152 | 3621246 | 4343922 | 2 |
| −1 | 4086038 | 5779074 | 4555233 | 4806782 | 4 |
| −2 | 4295861 | 4126418 | 4707699 | 4376659 | 2 |
| −3 | 4397869 | 4804046 | 3922702 | 4374872 | 2 |
| Positive control = 100% survival | 26848160 | 28090710 | 31197133 | 28712001 | 100 |
| Negative control = 0% survival | 4158960 | 3585956 | 4047970 | 3930962 | 0 |
| [Anidulafungin] log μM | | | | | |
| 0.9542425 | 9960942 | 10967130 | 15364830 | 12097634 | 35 |
| 0.90309 | 15350400 | 11785650 | 7401575 | 11512542 | 32 |
| 0.845098 | 10949560 | 9736722 | 8273113 | 9653132 | 25 |
| 0.7781513 | 10219130 | 11308900 | 8342703 | 9956911 | 26 |
| 0.69897 | 10033620 | 4718363 | 7321110 | 7357698 | 16 |
| 0.60206 | 7387656 | 4239781 | 4439823 | 5355753 | 7 |
| 0.4771213 | 5124858 | 4212586 | 3823154 | 4386866 | 4 |
| 0.39794 | 7911533 | 3661322 | 9914104 | 7162320 | 15 |
| 0.30103 | 6944934 | 4307906 | 5211398 | 5488079 | 8 |
| 0.1760913 | 4125220 | 3558016 | 4929089 | 4204108 | 3 |
| 0 | 2763556 | 3715544 | 3395182 | 3291427 | −1 |
| −0.154902 | 3628425 | 3463582 | 3208621 | 3433543 | 0 |
| −0.30103 | 2638281 | 3646882 | 3842217 | 3375793 | −1 |
| −0.5228788 | 3892260 | 3780606 | 4016223 | 3896363 | 2 |
| −1 | 3282790 | 3299018 | 4299152 | 3626987 | 0 |
| −2 | 5018485 | 4417533 | 3450400 | 4295473 | 3 |
| −3 | 2824954 | 3274736 | 3773899 | 3291196 | −1 |
| Positive control = 100% survival | 29653885 | 27463825 | 27338953 | 28152221 | 100 |
| Negative control = 0% survival | 3651189 | 3453359 | 3450955 | 3518501 | 0 |

Figure 6A:
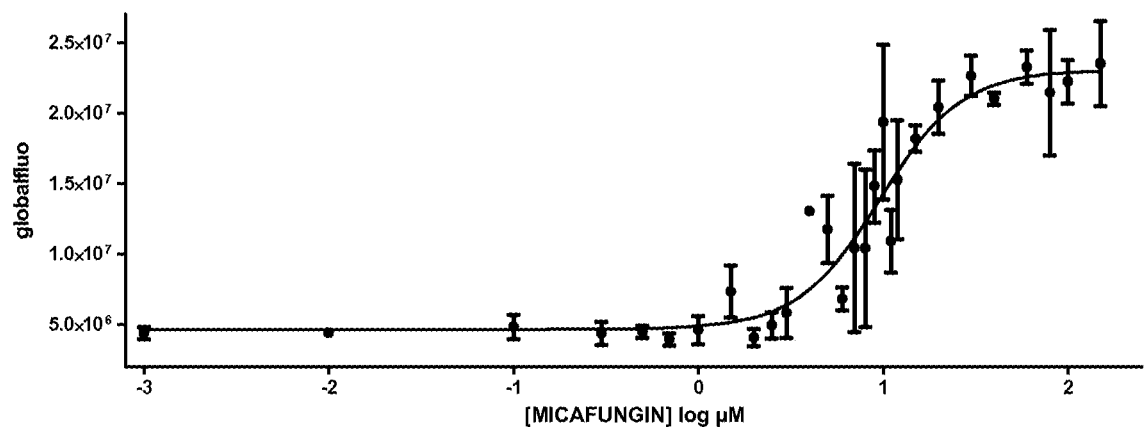
FIG. 6A and FIG. 6B represents the effects of micafungin and anidulafungin on rat renal glomerular endothelial cell survival in an in vitro model of oxygen and nutrient deprivation.
Figure 6B:
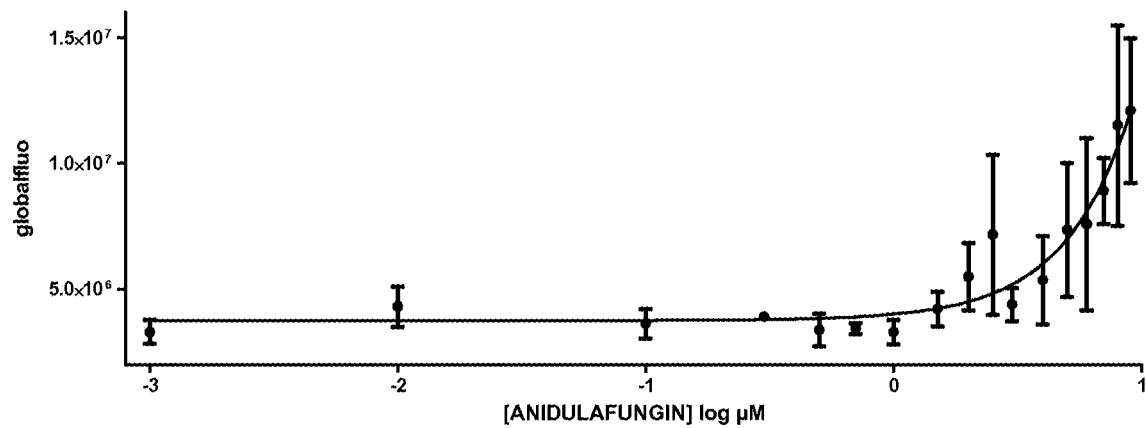

These results are presented graphically in FIGS. 6A and 6B; Micafungin=FIG. 6A; Anidulafungin=FIG. 6B.

Conclusion:

Due to their protective effect against oxygen and nutrient deprivation stress on rat renal glomerular endothelial cells, anidulafungin and micafungin according to the invention are thus shown to be useful as cytoprotective agents, in particular in the protection of animal renal cells against oxygen and nutrient deprivation, and especially in protection against ischemia reperfusion processes.

EXAMPLE 7: EFFECT OF MICAFUNGIN AND ANIDULAFUNGIN ON THE SURVIVAL OF BOVINE ENDOTHELIAL BRAIN CELLS IN AN IN VITRO MODEL OF OXYGEN AND NUTRIENT DEPRIVATION

| | Globalfluo assay 1 | Globalfluo assay 2 | Globalfluo assay 3 | Mean globalfluo | Survival rate (%) |
|---|---|---|---|---|---|
| [Micafungin] log μM | | | | | |
| 1.477121 | 2506989 | 2361926 | 2557219 | 2475378 | 79 |
| 1.30103 | 3526958 | 3025877 | 3586726 | 3379854 | 123 |
| 1.176091 | 2994828 | 3496204 | 3106542 | 3199191 | 114 |
| 1.079181 | 2865371 | 2913567 | 3561196 | 3113378 | 110 |
| 1 | 3519337 | 3058877 | 3179364 | 3252526 | 117 |
| 0.90309 | 3787727 | 1942995 | 2729816 | 2820179 | 96 |
| 0.7781513 | 1732851 | 1742799 | 1796080 | 1757243 | 44 |
| 0.4771213 | 2106751 | 1655153 | 1618365 | 1793423 | 46 |
| 0 | 1369504 | 1354112 | 1230715 | 1318110 | 23 |
| −0.5228788 | 1907644 | 993296 | 1867099 | 1589346 | 36 |
| −1 | 1108584 | 1249769 | 1224251 | 1194201 | 17 |
| −2 | 1778372 | 817005 | 1173090 | 1256156 | 20 |
| Positive control = 100% survival | 3322217 | 3108047 | 2299430 | 2909898 | 100 |
| Negative control = 0% survival | 820285 | 749153 | 995756 | 855065 | 0 |
| [Anidulafungin] log μM | | | | | |
| 0.60206 | 4710709 | 5014887 | 4901610 | 4875735 | 248 |
| 0.30103 | 2455048 | 2409886 | 4507112 | 3124015 | 145 |
| 0.1760913 | 2348228 | 1617378 | 1887981 | 1951196 | 77 |
| 0 | 941644 | 1153883 | 1374585 | 1156704 | 30 |
| −0.1249387 | 1165160 | 919370 | 944308 | 1009613 | 22 |
| −0.30103 | 744687 | 1045135 | 678965 | 822929 | 11 |
| −0.5228788 | 800327 | 708910 | 845212 | 784816 | 8 |
| −1 | 649447 | 1235676 | 807779 | 897634 | 15 |
| −2 | 664396 | 532817 | 541230 | 579481 | −4 |
| Positive control = 100% survival | 2150719 | 2705624 | 2196023 | 2350789 | 100 |
| Negative control = 0% survival | 589297 | 773950 | 557838 | 640362 | 0 |

Figure 7A:
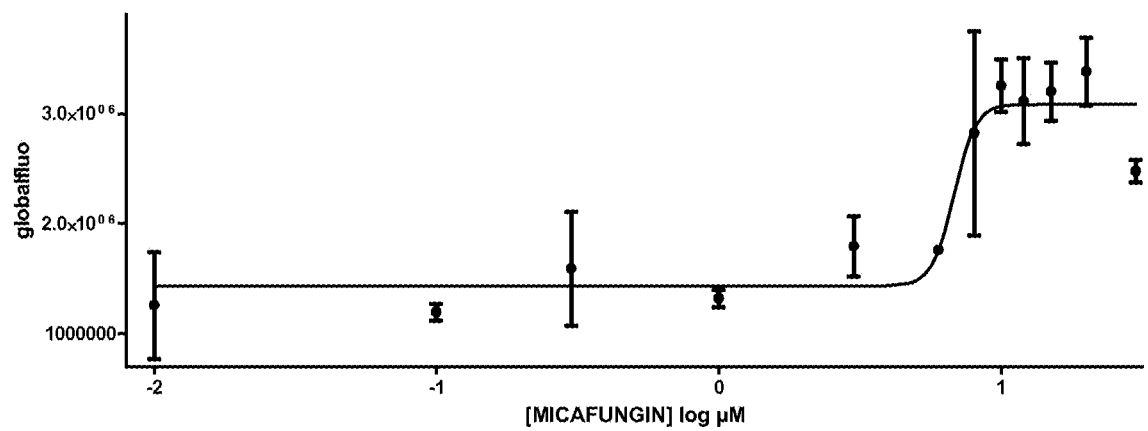
FIG. 7A and FIG. 7B represents the effects of micafungin and anidulafungin on bovine endothelial brain cell survival in an in vitro model of oxygen and nutrient deprivation.
Figure 7B:
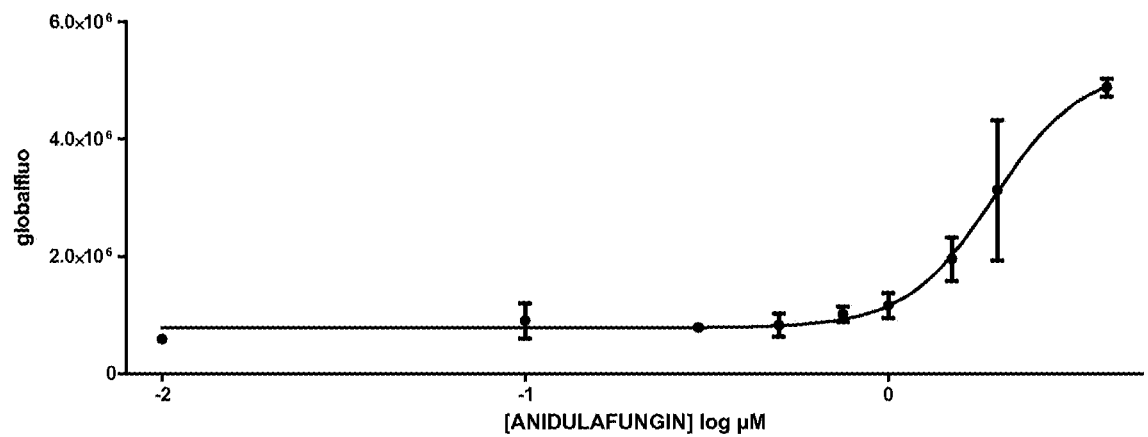

These results are presented graphically in FIGS. 7A and 7B; Micafungin=FIG. 7A; Anidulafungin=FIG. 7B.

Conclusion:

Due to their protective effect against oxygen and nutrient stress deprivation on bovine endothelial brain cells, the anidulafungin and the micafungin according to the invention are thus shown to be useful as cytoprotective agents, in particular in the protection of animal brain cells against deprivation of oxygen and nutrients, and in particular in the protection against ischemia reperfusion processes.

II) Effect of the compounds on rat survival.

Protocol

To demonstrate the cytoprotective action of micafungin and anidulafungin, the applicant studied their in vivo activity on Sprague Dawley rats in an in vivo model of acute renal failure (ARF). The protocol is similar to the one described by Narayan P et al, Am J Physiol Renal Physiol, 311(2): F352-61, 2016 and was approved by an ethics committee. In summary, general anesthesia is induced in male Sprague Dawley rats (250-300 g) using sodium pentobarbital (60 mg/kg, ip) instead of ketamine/xylazine in the protocol described by Narayan P et al, Am J Physiol Renal Physiol, 311 (2): F352-61, 2016. A skin incision is made on the dorsal surface and the left kidney is exposed by incisions on the flank. The left renal pedicle is then isolated and clamped for 60 minutes using atraumatic vascular clamps. The kidneys are replaced in the abdominal cavity to maintain temperature and the incision is covered with gauze soaked in 0.9% saline. After the ischemia time (60 minutes), the clamps are released to begin reperfusion. Reperfusion is monitored (kidney color change) for 1 to 2 minutes and physiological saline (1 mL) is administered to prevent dehydration. Next, a right kidney nephrectomy is performed and the incisions are closed with sutures. The animals are kept at approximately 37° C. using a thermoregulated system during the operation. Buprenorphine (0.2 mg/kg sc) is administered before the animals are returned to their cages and once a day until 4 days after reperfusion.

Animals are observed twice daily for general clinical signs and mortality up to 7 days after reperfusion. Animals are sacrificed if ethical endpoints indicating acute pain or distress are reached using an assessment method adapted to the guidelines of Morton and Griffiths (1985). In particular, the general condition of the animal is observed by assessing its weight, appearance, locomotion and posture, behavior and any other clinical signs considered predictive of death.

Blood collection is performed at D-2, D-3, D-5 and D-7 to measure creatinine and urea levels in plasma samples using an ABX Pentra 400 (HORIBA) clinical chemistry analyzer. At the end of the protocol (D-7), all animals are sacrificed and the left kidney is collected, weighed and fixed.

The compounds Micafungin (0.25 mg/kg), Anidulafungin (0.35 mg/kg) or the combination of the compounds Micafungin (0.25 mg/kg) and Allopurinol (3 mg/kg) are administered solubilized in physiological saline as a single intravenous injection into the tail vein 60 (±15) minutes before the onset of ischemia. The volume of administration of the compounds is determined on the basis of the body weight (2 mL/kg) of each animal.

The control groups in this experiment are represented by a sham group (operated on but receiving neither vascular clamp nor treatment) and an operated on group receiving the saline vehicle (control group).

This experimental model of unilateral renal ischemia followed by contralateral nephrectomy in rodents allows access to a warm ischemia followed by reperfusion which simulates what a kidney encounters when blood flow is stopped or disrupted during surgery for example. This model leads to acute tubular lesions that can lead to the death of the animal and mimics the clinical scenario of acute renal failure.

For each experiment the curve of the number of surviving animals versus the number of days post-ischemia-reperfusion (Kaplan-Meier curve) is shown. The x-axis is graduated from the first day =0 to the seventh day =6 The y-axis is graduated from 0% to 100% of the initial population of the analyzed group. The tests for micafungin alone, anidulafungin alone, allopurinol alone or in combination with micafungin in this animal model of acute renal failure are shown in FIGS. 8 and 9.

EXAMPLE 8: EFFECT OF MICAFUNGIN OF AND OF ANIDULAFUNGIN ON THE SURVIVAL OF ANIMALS IN A MODEL OF ACUTE RENAL FAILURE IN THE RAT

The SHAM group (n=6) is represented by a dashed line ending with a value of 100%.

The control group (n=14) is represented by a continuous line that ends with a value of 29%.

The Micafungin group (0.25 mg/kg) (n=12) is represented by a grey hatched line ending with a value of 67%.

The Anidulafungin (0.35 mg/kg) group (n=8) is represented by a broken line alternating a dash and a dot ending with a value of 75%.

Figure 8A:
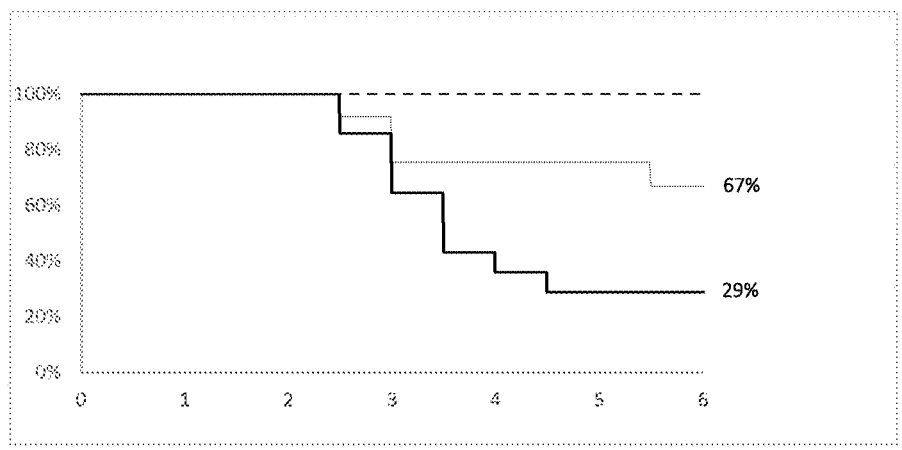
FIG. 8A and FIG. 8B represents the effects of micafungin and anidulafungin on the survival of Sprague Dawley rats in an acute renal failure model.
Figure 8B:
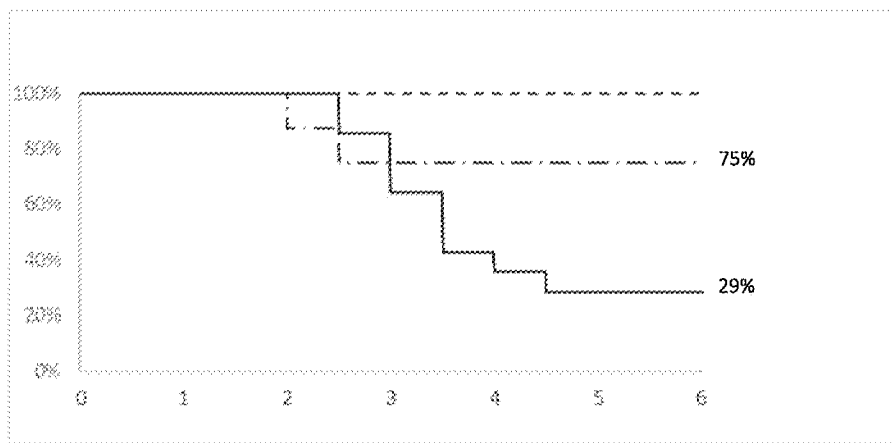
Figure 9:
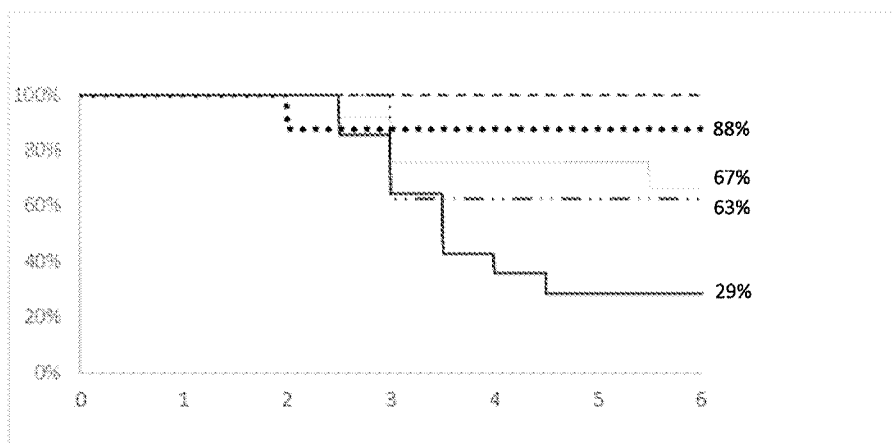
FIG. 9 represents the effects of micafungin in combination with allopurinol on the survival of Sprague Dawley rats in an acute renal failure model.

These results are presented graphically in FIGS. 8A and 8B.

Conclusion: Due to their protective effect against the stress of ischemia/reperfusion in rats, the anidulafungin and the micafungin according to the invention are thus shown to be useful as cytoprotective agents, in particular in the survival of the rats against the effects of warm ischemia followed by reperfusion, and especially in acute renal failure.

EXAMPLE 9: EFFECT OF MICAFUNGIN OF AND OF ALLOPURINOL ALONE OR IN COMBINATION ON THE SURVIVAL OF ANIMALS IN A MODEL OF ACUTE RENAL FAILURE IN THE RAT

The SHAM group (n=6) is represented by a dashed line ending with a value of 100%.

The control group (n=14) is represented by a continuous line that ends with a value of 29%.

The Micafungin group (0.25 mg/kg) (n=12) is represented by a grey hatched line ending with a value of 67%.

The Allopurinol group (3 mg/kg) (n=8) is represented by a broken line alternating a dash and two dots ending with a value of 63%.

The Micafungin (0.25 mg/kg)+Allopurinol (3 mg/kg) group (n=8) is represented by a dotted line ending with a value of 88%.

These results are presented graphically in FIG. 9.

Conclusion: Due to their protective effect against the stress of ischemia/reperfusion in rats, micafungin alone and even more so when combined with Allopurinol according to the invention are thus shown to be useful as cytoprotective agents, in particular in the survival of rats against the effects of hot ischemia followed by reperfusion, and especially in acute renal failure.

The invention claimed is:

1. A method for treating psoriasis, comprising administering to a subject in need thereof and in the absence of fungal infection a compound of the echinocandin family, or a salt, ester or ester salt thereof, as a cytoprotective drug.

2. The method of claim 1, wherein the compound of the echinocandin family, or a salt, ester or ester salt thereof, is administered in the form of a pharmaceutical composition comprising at least one compound of the echinocandin family, or a salt, ester or ester salt thereof, as a cytoprotective drug, and a pharmaceutically acceptable excipient or carrier.

3. The method of claim 2, wherein the pharmaceutical composition further comprises at least one other ingredient that is therapeutically active either on the same pathology or on a different pathology.

4. The method of claim 3, wherein said at least one other ingredient that is therapeutically active is a hypo-uricemiant compound.

5. The method of claim 1, wherein the compound of the echinocandin family is selected from caspofungin, micafungin, anidulafungin, cilofungin, enfumafungin, arundifungin, echinocandin B, biafungin, CD101 IV or rezafungin, pneumocandins, arbocandins and papulacandins.

6. The method of claim 4, wherein said at least one other ingredient that is therapeutically active is a hypo-uricemiant compound selected from the group consisting of a xanthine oxidase inhibitor, probenecid, benzbromarone, urate oxidase, and a mixture thereof.

7. The method of claim 6, wherein said at least one other ingredient that is a xanthine oxidase inhibitor is selected from the group consisting of allopurinol, febuxostat, and a mixture thereof.

8. The method of claim 7, wherein said at least one other ingredient is allopurinol.

9. The method of claim 5, wherein the compound of the echinocandin family is selected from the group consisting of caspofungin, micafungin, anidulafungin, a salt thereof, an ester thereof, and an ester salt thereof.

* * * * *